(12) United States Patent
To et al.

(10) Patent No.: US 9,198,679 B2
(45) Date of Patent: Dec. 1, 2015

(54) ATHERECTOMY DEVICES AND METHODS

(75) Inventors: John T To, Newark, CA (US); Paul Escudero, Redwood City, CA (US); Christopher James Danek, San Carlos, CA (US)

(73) Assignee: AtheroMed, Inc., Menlo Park, CA (US)

( * ) Notice: Subject to any disclaimer, the term of this patent is extended or adjusted under 35 U.S.C. 154(b) by 179 days.

(21) Appl. No.: 13/545,879

(22) Filed: Jul. 10, 2012

(65) Prior Publication Data
US 2013/0085515 A1 Apr. 4, 2013

Related U.S. Application Data

(63) Continuation of application No. 12/384,970, filed on Apr. 10, 2009, now Pat. No. 8,236,016, and a continuation-in-part of application No. 12/288,593, filed on Oct. 22, 2008, now Pat. No. 8,070,762.

(60) Provisional application No. 61/043,998, filed on Apr. 10, 2008, provisional application No. 60/981,735, filed on Oct. 22, 2007.

(51) Int. Cl.
*A61B 17/22* (2006.01)
*A61B 17/3207* (2006.01)
(Continued)

(52) U.S. Cl.
CPC ......... *A61B 17/22* (2013.01); *A61B 17/320758* (2013.01); *A61B 2017/00309* (2013.01); *A61B 2017/22038* (2013.01); *A61B 2017/22047* (2013.01); *A61B 2017/22048* (2013.01); *A61B 2017/22068* (2013.01); *A61B 2017/22082* (2013.01); *A61B 2017/320775* (2013.01); *A61M 25/0133* (2013.01); *A61M 25/0136* (2013.01);
(Continued)

(58) Field of Classification Search
CPC .................. A61B 17/3207; A61B 17/32075; A61B 17/320758; A61B 17/320783; A61B 17/22; A61B 2017/003; A61B 2017/00309; A61B 2017/00318; A61B 2017/00323; A61M 25/0147; A61M 25/0152; A61M 25/0133; A61M 25/0136; A61M 25/0138
USPC .......... 606/159, 151, 127, 170, 180; 600/141, 600/143; 604/510, 528, 523
See application file for complete search history.

(56) References Cited

U.S. PATENT DOCUMENTS

| 3,358,472 A | 12/1967 | Klipping |
| 4,167,944 A | 9/1979 | Banko |
| 4,445,509 A | 5/1984 | Auth |

(Continued)

FOREIGN PATENT DOCUMENTS

| EP | 0 817 594 B1 | 6/2002 |
| EP | 0 817 595 B1 | 6/2002 |

(Continued)

OTHER PUBLICATIONS

Ex-Parte Quayle Action mailed on Mar. 30, 2012, for U.S. Appl. No. 11/567,715, filed Dec. 6, 2006, 6 pages.

(Continued)

*Primary Examiner* — David C Eastwood
(74) *Attorney, Agent, or Firm* — Thomas C. Meyers; Brown Rudnick LLP

(57) ABSTRACT

The devices and methods generally relate to treatment of occluded body lumens. In particular, the present devices and method relate to removal of the occluding material from the blood vessels as well as other body lumens.

7 Claims, 28 Drawing Sheets

(51) Int. Cl.
    *A61M 25/01*      (2006.01)
    *A61B 17/00*      (2006.01)
(52) U.S. Cl.
    CPC ........ *A61M 25/0138* (2013.01); *A61M 25/0147*
             (2013.01); *A61M 25/0152* (2013.01)

(56) References Cited

U.S. PATENT DOCUMENTS

| | | |
|---|---|---|
| 4,598,710 A | 7/1986 | Kleinberg et al. |
| 4,631,052 A | 12/1986 | Kensey |
| 4,669,469 A | 6/1987 | Gifford, III et al. |
| 4,690,140 A | 9/1987 | Mecca |
| 4,696,667 A | 9/1987 | Masch |
| 4,770,652 A | 9/1988 | Mahurkar |
| 4,790,812 A | 12/1988 | Hawkins, Jr. et al. |
| 4,804,364 A | 2/1989 | Dieras et al. |
| 4,808,153 A | 2/1989 | Parisi |
| 4,844,064 A | 7/1989 | Thimsen et al. |
| 4,857,045 A | 8/1989 | Rydell |
| 4,857,046 A | 8/1989 | Stevens et al. |
| 4,886,490 A | 12/1989 | Shiber |
| 4,887,599 A | 12/1989 | Muller |
| 4,894,051 A | 1/1990 | Shiber |
| 4,911,148 A | 3/1990 | Sosnowski et al. |
| 4,950,277 A | 8/1990 | Farr |
| 4,994,067 A | 2/1991 | Summers |
| 5,074,841 A | 12/1991 | Ademovic et al. |
| 5,100,426 A | 3/1992 | Nixon |
| 5,114,399 A | 5/1992 | Kovalcheck |
| 5,231,989 A | 8/1993 | Middleman et al. |
| 5,242,461 A | 9/1993 | Kortenbach et al. |
| 5,267,955 A | 12/1993 | Hanson |
| 5,282,813 A | 2/1994 | Redha |
| 5,312,427 A | 5/1994 | Shturman |
| 5,314,438 A | 5/1994 | Shturman |
| 5,320,635 A | 6/1994 | Smith |
| 5,356,418 A | 10/1994 | Shturman |
| 5,358,472 A | 10/1994 | Vance et al. |
| 5,360,432 A | 11/1994 | Shturman |
| 5,370,609 A | 12/1994 | Drasler et al. |
| 5,372,587 A | 12/1994 | Hammerslag et al. |
| 5,409,454 A | 4/1995 | Fischell et al. |
| 5,423,799 A | 6/1995 | Shiu |
| 5,429,604 A | 7/1995 | Hammersmark et al. |
| 5,429,617 A | 7/1995 | Hammersmark et al. |
| 5,431,173 A | 7/1995 | Chin et al. |
| 5,456,680 A | 10/1995 | Taylor et al. |
| 5,474,532 A | 12/1995 | Steppe |
| 5,489,291 A | 2/1996 | Wiley |
| 5,501,653 A | 3/1996 | Chin |
| 5,520,609 A | 5/1996 | Moll et al. |
| 5,529,580 A | 6/1996 | Kusunoki et al. |
| 5,540,706 A | 7/1996 | Aust et al. |
| 5,554,163 A | 9/1996 | Shturman |
| 5,556,408 A | 9/1996 | Farhat |
| 5,569,197 A | 10/1996 | Helmus et al. |
| 5,584,843 A | 12/1996 | Wulfman et al. |
| 5,618,294 A | 4/1997 | Aust et al. |
| 5,626,562 A | 5/1997 | Castro |
| 5,632,755 A | 5/1997 | Nordgren et al. |
| 5,634,883 A | 6/1997 | Chin et al. |
| 5,643,178 A | 7/1997 | Moll et al. |
| 5,643,251 A | 7/1997 | Hillsman et al. |
| 5,643,297 A | 7/1997 | Nordgren et al. |
| 5,643,298 A | 7/1997 | Nordgren et al. |
| 5,649,941 A | 7/1997 | Lary |
| 5,665,062 A | 9/1997 | Houser |
| 5,665,098 A | 9/1997 | Kelly et al. |
| 5,669,926 A | 9/1997 | Aust et al. |
| 5,690,634 A | 11/1997 | Muller et al. |
| 5,690,643 A | 11/1997 | Wijay |
| 5,695,506 A | 12/1997 | Pike et al. |
| 5,716,327 A | 2/1998 | Warner et al. |
| 5,725,543 A | 3/1998 | Redha |
| 5,728,129 A | 3/1998 | Summers |
| 5,733,297 A | 3/1998 | Wang |
| 5,743,456 A | 4/1998 | Jones et al. |
| 5,746,758 A | 5/1998 | Nordgren et al. |
| 5,755,731 A | 5/1998 | Frinberg |
| 5,766,196 A | 6/1998 | Griffiths |
| 5,782,834 A | 7/1998 | Lucey et al. |
| 5,820,592 A | 10/1998 | Hammerslag |
| 5,843,103 A | 12/1998 | Wulfman |
| 5,851,208 A | 12/1998 | Trolt |
| 5,851,212 A * | 12/1998 | Zirps et al. .................... 606/167 |
| 5,873,882 A | 2/1999 | Straub et al. |
| 5,876,414 A | 3/1999 | Straub |
| 5,882,329 A | 3/1999 | Patterson et al. |
| 5,882,333 A * | 3/1999 | Schaer et al. .............. 604/95.01 |
| 5,895,399 A | 4/1999 | Barbut et al. |
| 5,897,566 A | 4/1999 | Shturman et al. |
| 5,902,263 A | 5/1999 | Patterson et al. |
| 5,902,313 A | 5/1999 | Redha |
| 5,941,869 A | 8/1999 | Patterson et al. |
| 5,941,893 A | 8/1999 | Saadat |
| 6,001,112 A | 12/1999 | Taylor |
| 6,015,420 A | 1/2000 | Wulfman et al. |
| 6,027,514 A | 2/2000 | Stine et al. |
| 6,042,593 A | 3/2000 | Storz et al. |
| 6,048,339 A * | 4/2000 | Zirps et al. .................... 604/525 |
| 6,053,923 A | 4/2000 | Veca et al. |
| 6,066,153 A | 5/2000 | Lev |
| 6,080,170 A | 6/2000 | Nash et al. |
| 6,090,118 A | 7/2000 | McGuckin, Jr. |
| 6,132,444 A | 10/2000 | Shturman et al. |
| 6,139,557 A | 10/2000 | Passafaro et al. |
| 6,142,955 A | 11/2000 | Farascioni et al. |
| 6,146,395 A | 11/2000 | Kanz et al. |
| 6,152,938 A | 11/2000 | Curry |
| 6,156,046 A | 12/2000 | Passafaro et al. |
| 6,165,209 A | 12/2000 | Patterson et al. |
| 6,206,898 B1 | 3/2001 | Honeycutt et al. |
| 6,238,405 B1 | 5/2001 | Findlay, III et al. |
| 6,241,744 B1 | 6/2001 | Imran et al. |
| 6,258,098 B1 | 7/2001 | Taylor et al. |
| 6,264,630 B1 | 7/2001 | Mickley et al. |
| 6,299,622 B1 | 10/2001 | Snow et al. |
| 6,319,242 B1 | 11/2001 | Patterson et al. |
| 6,355,027 B1 | 3/2002 | Le et al. |
| 6,371,928 B1 | 4/2002 | McFann et al. |
| 6,406,442 B1 | 6/2002 | McFann et al. |
| 6,451,036 B1 | 9/2002 | Heitzmann et al. |
| 6,454,779 B1 | 9/2002 | Taylor |
| 6,482,215 B1 | 11/2002 | Shiber |
| 6,482,217 B1 | 11/2002 | Pintor et al. |
| 6,494,890 B1 | 12/2002 | Shturman et al. |
| 6,497,711 B1 | 12/2002 | Plaia et al. |
| 6,554,846 B2 | 4/2003 | Hamilton et al. |
| 6,562,049 B1 | 5/2003 | Norlander et al. |
| 6,565,588 B1 | 5/2003 | Clement et al. |
| 6,572,630 B1 | 6/2003 | McGuckin, Jr. et al. |
| 6,579,299 B2 | 6/2003 | McGuckin, Jr. et al. |
| 6,596,005 B1 | 7/2003 | Kanz et al. |
| 6,602,264 B1 | 8/2003 | McGuckin, Jr. |
| 6,623,495 B2 | 9/2003 | Findlay, III et al. |
| 6,629,953 B1 | 10/2003 | Boyd |
| 6,638,233 B2 | 10/2003 | Corvi et al. |
| 6,638,288 B1 | 10/2003 | Shturman et al. |
| RE38,335 E | 11/2003 | Aust et al. |
| 6,656,195 B2 | 12/2003 | Peters et al. |
| 6,666,854 B1 | 12/2003 | Lange |
| 6,666,874 B2 | 12/2003 | Heitzmann et al. |
| 6,702,830 B1 | 3/2004 | Demarais et al. |
| 6,758,851 B2 | 7/2004 | Shiber |
| 6,790,215 B2 | 9/2004 | Findlay, III et al. |
| 6,800,085 B2 | 10/2004 | Selmon et al. |
| 6,808,531 B2 | 10/2004 | Lafontaine et al. |
| 6,818,001 B2 | 11/2004 | Wulfman et al. |
| 6,818,002 B2 | 11/2004 | Shiber |
| 6,830,577 B2 | 12/2004 | Nash et al. |
| 6,843,797 B2 | 1/2005 | Nash et al. |
| 6,860,235 B2 | 3/2005 | Anderson et al. |
| 6,876,414 B2 | 4/2005 | Hara et al. |

(56) References Cited

U.S. PATENT DOCUMENTS

| | | | |
|---|---|---|---|
| 6,936,056 B2 | 8/2005 | Nash et al. | |
| 6,997,934 B2 | 2/2006 | Snow et al. | |
| 7,008,375 B2 | 3/2006 | Weisel | |
| 7,025,751 B2 | 4/2006 | Silva et al. | |
| 7,033,357 B2 | 4/2006 | Baxter et al. | |
| 7,037,316 B2 | 5/2006 | McGuckin, Jr. et al. | |
| RE39,152 E | 6/2006 | Aust et al. | |
| 7,172,610 B2 | 2/2007 | Heitzmann et al. | |
| 7,235,088 B2 | 6/2007 | Pintor et al. | |
| 7,344,546 B2 | 3/2008 | Wulfman et al. | |
| 7,344,548 B2 | 3/2008 | Toyota et al. | |
| 7,381,198 B2 | 6/2008 | Noriega et al. | |
| 7,399,307 B2 | 7/2008 | Evans et al. | |
| 7,479,147 B2 | 1/2009 | Honeycutt et al. | |
| 7,534,249 B2 | 5/2009 | Nash et al. | |
| 7,666,161 B2 | 2/2010 | Nash et al. | |
| 7,981,128 B2 | 7/2011 | To et al. | |
| 8,007,506 B2 | 8/2011 | To et al. | |
| 8,070,762 B2 | 12/2011 | Escudero et al. | |
| 8,236,016 B2 * | 8/2012 | To et al. | 606/159 |
| 8,337,516 B2 * | 12/2012 | Escudero et al. | 606/159 |
| 2002/0007190 A1 | 1/2002 | Wulfman et al. | |
| 2002/0029057 A1 | 3/2002 | McGuckin, Jr. | |
| 2002/0077642 A1 | 6/2002 | Patel et al. | |
| 2002/0169467 A1 | 11/2002 | Heitzmann et al. | |
| 2002/0198550 A1 | 12/2002 | Nash et al. | |
| 2003/0018346 A1 | 1/2003 | Follmer et al. | |
| 2003/0078606 A1 | 4/2003 | Lafontaine et al. | |
| 2003/0100911 A1 | 5/2003 | Nash et al. | |
| 2003/0114869 A1 | 6/2003 | Nash et al. | |
| 2003/0125758 A1 | 7/2003 | Simpson et al. | |
| 2003/0139802 A1 | 7/2003 | Wulfman et al. | |
| 2004/0006358 A1 | 1/2004 | Wulfman et al. | |
| 2004/0087988 A1 | 5/2004 | Heitzmann et al. | |
| 2004/0097995 A1 | 5/2004 | Nash et al. | |
| 2004/0102772 A1 | 5/2004 | Baxter et al. | |
| 2004/0147934 A1 | 7/2004 | Kiester | |
| 2004/0167553 A1 | 8/2004 | Simpson et al. | |
| 2004/0167554 A1 | 8/2004 | Simpson et al. | |
| 2004/0181249 A1 | 9/2004 | Torrance et al. | |
| 2004/0220519 A1 | 11/2004 | Wulfman et al. | |
| 2004/0230212 A1 | 11/2004 | Wulfman | |
| 2004/0230213 A1 | 11/2004 | Wulfman et al. | |
| 2004/0235611 A1 | 11/2004 | Nistal | |
| 2004/0236312 A1 | 11/2004 | Nistal et al. | |
| 2004/0243162 A1 | 12/2004 | Wulfman et al. | |
| 2005/0004585 A1 | 1/2005 | Hall et al. | |
| 2005/0020974 A1 | 1/2005 | Noriega et al. | |
| 2005/0059990 A1 | 3/2005 | Ayala et al. | |
| 2005/0113853 A1 | 5/2005 | Noriega et al. | |
| 2005/0149084 A1 | 7/2005 | Kanz et al. | |
| 2005/0177068 A1 | 8/2005 | Simpson | |
| 2005/0197661 A1 | 9/2005 | Carrison et al. | |
| 2005/0222519 A1 | 10/2005 | Simpson | |
| 2005/0240146 A1 | 10/2005 | Nash et al. | |
| 2006/0020327 A1 | 1/2006 | Lashinski et al. | |
| 2006/0229646 A1 | 10/2006 | Sparks | |
| 2006/0239982 A1 | 10/2006 | Simpson | |
| 2006/0241564 A1 * | 10/2006 | Corcoran et al. | 604/523 |
| 2007/0225739 A1 | 9/2007 | Pintor et al. | |
| 2007/0250000 A1 | 10/2007 | Magnin et al. | |
| 2007/0282303 A1 | 12/2007 | Nash et al. | |
| 2007/0282350 A1 | 12/2007 | Hernest | |
| 2007/0282358 A1 | 12/2007 | Remiszewski et al. | |
| 2008/0004643 A1 | 1/2008 | To et al. | |
| 2008/0004644 A1 | 1/2008 | To et al. | |
| 2008/0004645 A1 | 1/2008 | To et al. | |
| 2008/0004646 A1 | 1/2008 | To et al. | |
| 2008/0004647 A1 | 1/2008 | To et al. | |
| 2008/0045986 A1 | 2/2008 | To et al. | |
| 2008/0249364 A1 | 10/2008 | Korner | |
| 2009/0018565 A1 | 1/2009 | To et al. | |
| 2009/0018566 A1 | 1/2009 | Escudero et al. | |
| 2009/0018567 A1 | 1/2009 | Escudero et al. | |
| 2009/0024085 A1 | 1/2009 | To et al. | |
| 2009/0234378 A1 | 9/2009 | Escudero et al. | |
| 2010/0174302 A1 | 7/2010 | Heitzmann et al. | |
| 2010/0324567 A1 | 12/2010 | Root et al. | |
| 2010/0324576 A1 | 12/2010 | Pintor et al. | |
| 2011/0040315 A1 | 2/2011 | To et al. | |
| 2011/0112563 A1 | 5/2011 | To et al. | |
| 2011/0152906 A1 | 6/2011 | Escudero et al. | |
| 2011/0152907 A1 | 6/2011 | Escudero et al. | |
| 2011/0270289 A1 | 11/2011 | To et al. | |
| 2011/0301626 A1 | 12/2011 | To et al. | |
| 2012/0083810 A1 | 4/2012 | Escudero et al. | |

FOREIGN PATENT DOCUMENTS

| | | |
|---|---|---|
| EP | 1 176 915 B1 | 10/2005 |
| EP | 1 158 910 B1 | 10/2007 |
| EP | 1 315 460 B1 | 12/2007 |
| EP | 1 722 694 B1 | 5/2009 |
| EP | 1 870 044 B1 | 7/2009 |
| JP | 2001-522631 A | 11/2001 |
| WO | WO-95/21576 A1 | 8/1995 |
| WO | WO-99/23958 A1 | 5/1999 |
| WO | WO-99/35977 A1 | 7/1999 |
| WO | WO-00/54659 A1 | 9/2000 |
| WO | WO 0054659 A1 * | 9/2000 |
| WO | WO-2005/123169 A1 | 12/2005 |
| WO | WO-2008/005888 A2 | 1/2008 |
| WO | WO-2008/005888 A3 | 1/2008 |
| WO | WO-2008/005891 A2 | 1/2008 |
| WO | WO-2008/005891 A3 | 1/2008 |
| WO | WO-2009/005779 A1 | 1/2009 |
| WO | WO-2009/054968 A1 | 4/2009 |
| WO | WO-2009/126309 A2 | 10/2009 |
| WO | WO-2009/126309 A3 | 10/2009 |

OTHER PUBLICATIONS

Ex-Parte Quayle Action mailed on Mar. 30, 2012, for U.S. Appl. No. 12/215,721, filed Jun. 30, 2008, 6 pages.

Final Office Action mailed on Feb. 3, 2010, for U.S. Appl. No. 11/551,193, filed Oct. 19, 2006, 8 pages.

Final Office Action mailed on May 25, 2010, for U.S. Appl. No. 11/551,191, filed Oct. 19, 2006, 11 pages.

Final Office Action mailed on Mar. 11, 2011, for U.S. Appl. No. 11/771,865, filed Jun. 29, 2007, 8 pages.

Final Office Action mailed on Apr. 15, 2011, for U.S. Appl. No. 12/215,854, filed Jun. 30, 2008, 8 pages.

Final Office Action mailed on Apr. 20, 2011, for U.S. Appl. No. 12/215,855, filed Jun. 30, 2008, 9 pages.

Final Office Action mailed on Jul. 13, 2011, for U.S. Appl. No. 12/215,752, filed Jun. 30, 2008, 7 pages.

Final Office Action mailed on Dec. 22, 2011, for U.S. Appl. No. 11/567,715, filed Dec. 6, 2006, 6 pages.

Final Office Action mailed on Dec. 22, 2011, for U.S. Appl. No. 12/215,721, filed Jun. 30, 2008, 6 pages.

Final Office Action mailed on Mar. 22, 2012, for U.S. Appl. No. 11/551,191, filed Oct. 19, 2006, 5 pages.

Ikeno, F. et al. (2004). "Initial Experience with the Novel 6 Fr-Compatible System for Debulking De Novo Coronary Arterial Lesions," *Catheterization and Cardiovascular Interventions* 62:308-317.

International Preliminary Report on Patentability issued on Jan. 6, 2009, for PCT Patent Application No. PCT/US2007/072570, filed on Jun. 29, 2007, 4 pages.

International Preliminary Report on Patentability issued Jan. 6, 2009, for PCT Patent Application No. PCT/US2007/072574, filed on Jun. 29, 2007, 4 pages.

International Preliminary Report on Patentability issued on Jun. 30, 2010, for PCT Patent Application No. PCT/US2008/012012, filed on Oct. 22, 2008, 11 pages.

International Preliminary Report on Patentability issued on Aug. 6, 2010, for PCT Patent Application No. PCT/US2009/002253, filed on Apr. 10, 2009, 12 pages.

International Search Report mailed on Sep. 3, 2008, for PCT Patent Application No. PCT/US2007/72570, filed on Jun. 29, 2007, 1 page.

(56) References Cited

OTHER PUBLICATIONS

International Search Report mailed on Sep. 18, 2008, for PCT Patent Application No. PCT/US2007/072574, filed on Jun. 29, 2007, 1 page.
International Search Report mailed on Oct. 29, 2008, for PCT Patent Application No. PCT/US2008/08140, filed on Jun. 30, 2008, 1 page.
International Search Report mailed on Feb. 12, 2009, for PCT Patent Application No. PCT/US2008/12012, filed on Oct. 22, 2008, 1 page.
International Search Report mailed on Aug. 12, 2009, for PCT Patent Application No. PCT/US2009/02253, filed on Apr. 10, 2009, 1 page.
Kanjwal, M.K. et al. (2004). "Peripheral Arterial Disease—The Silent Killer," *JK-Practitioner* 11(4):225-232.
Nakamura, M. et al. (2002). "Efficacy and Feasibility of Helixcision for Debulking Neointimal Hyperplasia for In-Stent Restenosis," *Catheterization and Cardiovascular Interventions* 57:460-466.
Non-Final Office Action mailed on Apr. 3, 2009, for U.S. Appl. No. 11/551,193, filed Oct. 19, 2006, 7 pages.
Non-Final Office Action mailed on May 27, 2009, for U.S. Appl. No. 11/567,715, filed Dec. 6, 2006, 16 pages.
Non-Final Office Action mailed on Jul. 15, 2009, for U.S. No. 11/551,191, filed Oct. 19, 2006, 18 pages.
Non-Final Office Action mailed on Jun. 25, 2010, for U.S. Appl. No. 11/551,198, filed Oct. 19, 2006, 15 pages.
Non-Final Office Action mailed on Jun. 25, 2010, for U.S. Appl. No. 11/771,865, filed Jun. 29, 2007, 10 pages.
Non-Final Office Action mailed on Aug. 27, 2010, for U.S. Appl. No. 11/551,203, filed Oct. 19, 2006, 19 pages.
Non-Final Office Action mailed on Oct. 5, 2010, for U.S. Appl. No. 12/215,855, filed Jun. 30, 2008, 10 pages.
Non-Final Office action mailed on Oct. 5, 2010, for U.S. Appl. No. 12/215,752, filed Jun. 30, 2008, 8 pages.
Non-Final Office Action mailed on Oct. 12, 2010, for U.S. Appl. No. 12/215,854, filed Jun. 30, 2008, 11 pages.
Non-Final Office Action mailed on Apr. 14, 2011, for U.S. Appl. No. 12/215,721, filed Jun. 30. 2008, 9 pages.
Non-Final Office Action mailed on Aug. 4, 2011, for U.S. Appl. No. 11/551,191, filed Oct. 19, 2006, 6 pages.
Non-Final Office Action mailed on Aug. 4, 2011, for U.S. Appl. No. 11/567,715, filed Dec. 6, 2006, 9 pages.
Notice of Allowance mailed on Feb. 19, 2010, for U.S. Appl. No. 11/567,715, filed Dec. 6, 2006, 6 pages.
Notice of Allowance mailed on Jun. 18, 2010 for U.S. Appl. No. 11/567,715, filed Dec. 6, 2006, 6 pages.
Notice of Allowance mailed on Nov. 29, 2010, for U.S. Appl. No. 11/567,715, filed Dec. 6, 2006, 6 pages.
Notice of Allowance mailed on Dec. 10, 2010, for U.S. Appl. No. 11/551,193, filed Oct. 19, 2006, 7 pages.
Notice of Allowance mailed on Mar. 3, 2011, for U.S. Appl. No. 11/551,193, filed Oct. 19, 2006, 7 pages.
Notice of Allowance mailed on Jun. 3, 2011, for U.S. Appl. No. 11/551,203, filed Oct. 19, 2006, 10 pages.
Notice of Allowance mailed on Oct. 4, 2011, for U.S. Appl. No. 12/288,593, filed Oct. 22, 2008, 9 pages.
Notice of Allowance mailed on Dec. 13, 2011, for U.S. Appl. No. 12/384,970, filed Apr. 10, 2009, 11 pages.
Notice of Allowance mailed on Aug. 6, 2012, for U.S. Appl. No. 12/215,721, filed Jun. 30, 2008, 8 pages.
Notice of Allowance mailed on Aug. 22, 2012, for U.S. Appl. No. 13/309,986, filed Dec. 2, 2011, 10 pages.
Notice of Allowance mailed on Sep. 18, 2012, for U.S. Appl. No. 11/567,715, filed Dec. 6, 2006, 8 pages.
Supplementary European Search Report mailed on Jun. 20, 2011, for EP Patent Application No. 08779894.8, filed on Jun. 30, 2008, 7 pages.

\* cited by examiner

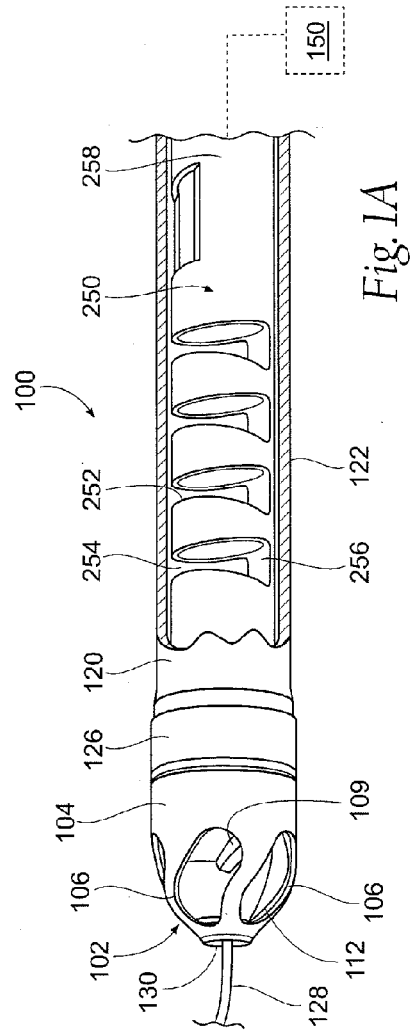
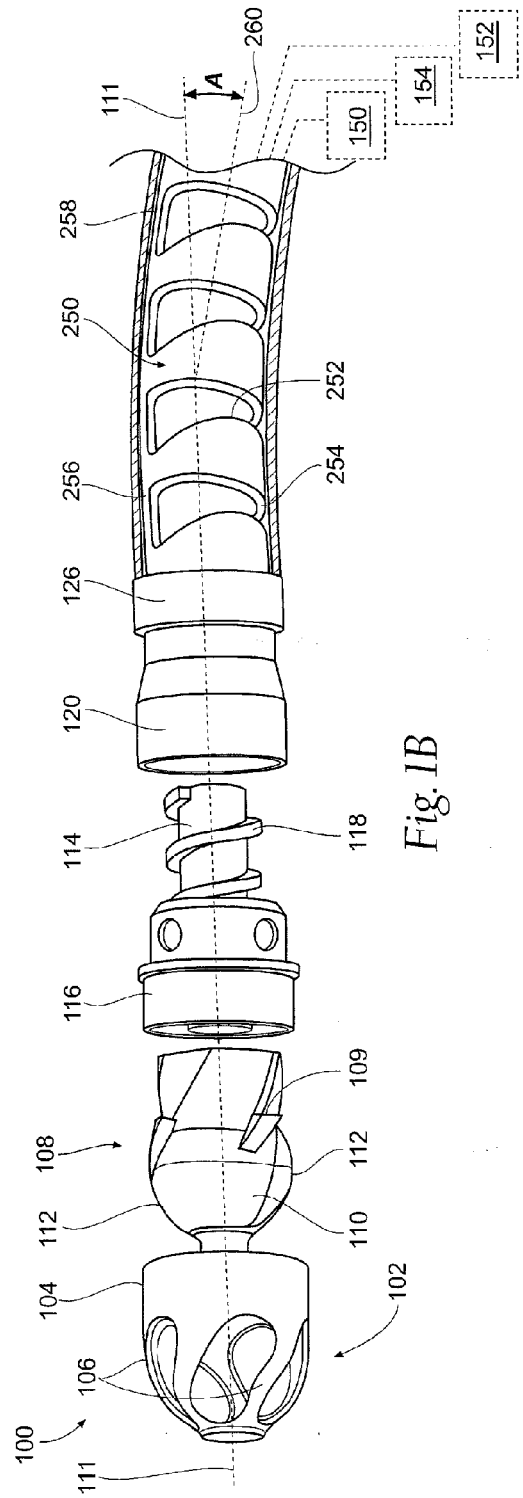

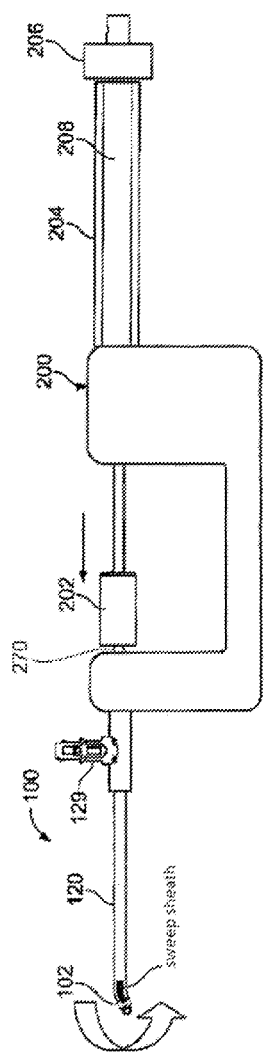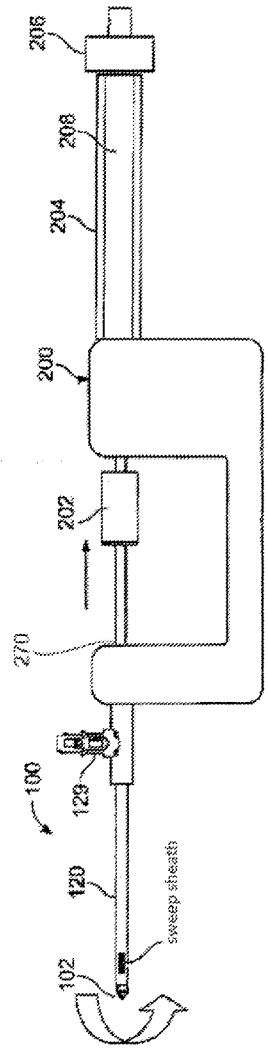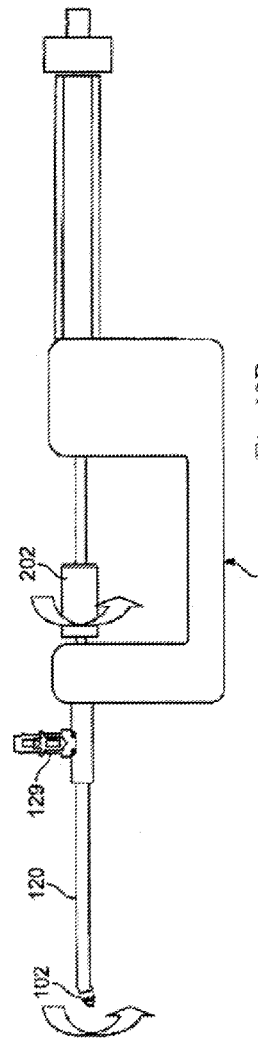

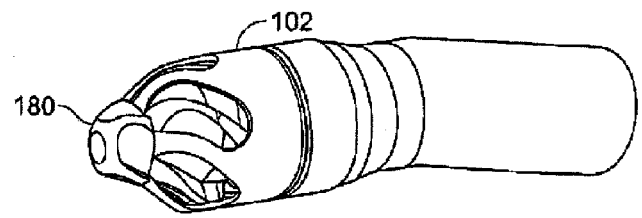
Fig. 13
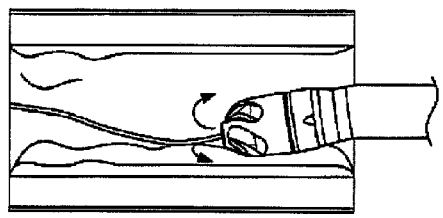 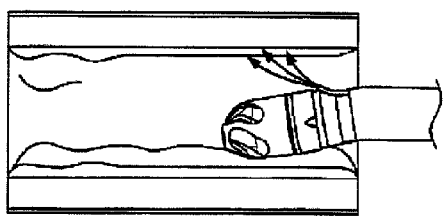
Fig. 14A    Fig. 14B
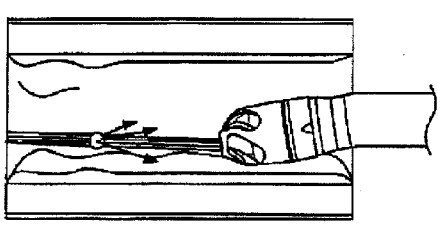 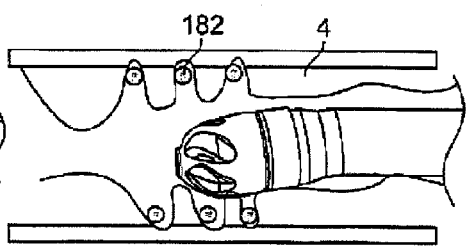
Fig. 14C    Fig. 15

ATHERECTOMY DEVICES AND METHODS

RELATED APPLICATIONS

This application is a continuation of U.S. patent application Ser. No. 12/384,970, filed Apr. 10, 2009 now U.S. Pat. No. 8,236,016, which claims priority to U.S. Provisional Application Ser. No. 61/043,998, filed Apr. 10, 2008 and is a continuation-in-part of U.S. patent application Ser. No. 12/288,593, filed Oct. 22, 2008 now U.S. Pat. No. 8,070,762, which claims priority to U.S. Provisional Application Ser. No. 60/981,735, filed Oct. 22, 2007, each of which are incorporated by reference in their entirety.

FIELD OF THE INVENTION

The devices and methods described below generally relate to treatment of occluded body lumens. In particular, the present devices and method relate to improved devices for removal of the occluding material from the blood vessels as well as other body parts. Such devices include features for improved positioning within the vessel or body part allowing for the targeted removal of tissue or sweeping of a cutting mechanism in an arc-shaped path.

BACKGROUND OF THE INVENTION

Atherosclerosis is a progressive disease. In this disease, lesions of the arteries are formed by accumulation of plaque and neointimal hyperplasia causing an obstruction of blood flow. Often plaque is friable and may dislodge naturally or during an endovascular procedure, leading to embolization of a downstream vessel.

Endovascular clearing procedures to reduce or remove the obstructions to restore luminal diameter allows for increased blood flow to normal levels are well known. Removing the plaque has the effect of removing diseased tissue and helps to reverse the disease. Maintaining luminal diameter for a period of time (several to many weeks) allows remodeling of the vessel from the previous pathological state to a more normal state. Finally, it is the goal of an endovascular to prevent short term complications such as embolization or perforation of the vessel and long term complications such as ischemia from thrombosis or restenosis.

Various treatment modalities may help to accomplish treatment goals. In atherectomy, plaque is cut away, or excised. Various configurations are used including a rotating cylindrical shaver or a fluted cutter. The devices may include shielding by a housing for safety. The devices may also remove debris via trapping the debris in the catheter, in a downstream filter, or aspirating the debris. In some cases a burr may be used instead of a cutter, particularly to grind heavily calcified lesions into very small particle sizes. Aspiration may also be used with a burr-type atherectomy device.

Balloon angioplasty is another type of endovascular procedure. Balloon angioplasty expands and opens the artery by both displacing the plaque and compressing it. Balloon angioplasty is known to cause barotrauma to the vessel from the high pressures required to compress the plaque. This trauma leads to an unacceptably high rate of restenosis. Furthermore, this procedure may not be efficient for treatment of elastic-type plaque tissue, where such tissue can spring back to occlude the lumen.

When clearing such obstructions it is desirable to protect the vessel wall or wall of the body lumen being cleared and to debulk substantially all of a lesion. In additional cases, the procedure that clears obstructions may also be coupled with placement of an implant within the lumen. For example, it may be desirable to deploy a stent to maintain patency of a vessel for a period of time and/or to achieve local drug delivery by having the stent elute a drug or other bioactive substance.

On their own, stents fail to perform well in the peripheral vasculature for a variety of reasons. A stent with the necessary structural integrity to supply sufficient radial force to reopen the artery often does not perform well in the harsh mechanical environment of the peripheral vasculature. For example, the peripheral vasculature encounters a significant amount of compression, torsion, extension, and bending. Such an environment may lead to stent failure (strut cracking, stent crushing, etc.) that eventually compromises the ability of the stent to maintain lumen diameter over the long-term. On the other hand, a stent that is able to withstand the harsh mechanical aspects of the periphery often will not supply enough radial force to open the vessel satisfactorily. In many cases, medical practitioners desire the ability to combine endovascular clearing procedures with stenting. Such stenting may occur prior to, after, or both before and after the endovascular clearing procedure.

Accordingly, a need remains for devices that allow for improved atherectomy devices that are able to navigate through tortous anatomy and clear materials from body lumens (such as blood vessels) where the device includes features to allow for a safe, efficient and controlled fashion of shaving or grinding material within the body lumen while minimizing procedure times. In addition, there remains a need for devices that allow steering of the distal portion of the device while navigating through tortuous anatomy. The ability to steer assists the physician in accessing tortuous anatomy and can further assist in delivering a guidewire into the entrance of angled or tortuous vessel bifurcation/segments. This is possible because variations of the steerable atherectomy catheter described herein can also function as a 'shuttle catheter', where the physician can aim the distal tip into the vessel to be accessed and advancing the guidewire into that vessel from within the catheter.

There also remains a need for devices that are configured to steer but will remain in a straight configuration when not being articulated. It is generally known that conventional catheters that take a shape often bias to one side either through repeated articulation or even after being left in packing for any given period of time. Accordingly, when such steering features are combined with tissue debulking devices, there remains a risk of injury if the tissue debulking device has an undesirable bend when the device is supposed to be in a straight configuration.

The debulking devices described herein address the problems noted above as well as provide significant improved features to allow a physician to steer a debulking device through tortuous anatomy and remove tissue at a target site.

SUMMARY OF THE INVENTION

Devices and methods described herein provide debulking devices having improved means of clearing obstructions within body lumens, especially the vasculature. In many variations the devices are suited for navigating through tortuous vessels. The features of the devices and methods allow for controlled removal of occlusive materials and navigation through tortuous and diseased vessels. In some variations, the methods and devices also have features to convey the materials away from the operative site without the need to remove the devices from the body lumen. Additional aspects include controlled rates of tissue removal as well as other safety features to prevent accidental cutting of the lumen wall. Although the devices and methods described herein discuss removal of materials from a blood vessel, in certain cases the devices and methods have applicability in other body parts as well. It should be noted that the variations and features of the devices described below may be incorporated selectively or in combination with a basic device configuration that includes a flexible body having a cutter, where the cutter includes a housing and a cutter, where the housing and cutter are able to rotate relative to each other. Variations include a cutter that rotates within the housing, a housing that rotates about the cutter, and combinations thereof.

One variation of the device described herein includes a device configured to remove material from body structures. The device may be a vascular device and have the required structure and configuration to navigate tortuous anatomy. Alternatively, the device may be a cutter that has features that are desired when used in other parts of the anatomy.

In any case, a variation of the device comprises a catheter body having a proximal end and a distal end and a catheter lumen extending therethrough, a cutting assembly including a housing and a rotatable cutter located within the housing, the cutting assembly affixed to the distal end of the catheter, where the housing includes at least one opening and the cutter includes at least one cutting edge, a sweep frame located adjacent to the cutting assembly, the sweep frame being coupled to the catheter and rotatable independently of the rotatable cutter, where the sweep frame comprises at least a weakened section on a first radial side such that compression of the sweep frame causes deflection towards the first radial side resulting in deflection of the distal end of the catheter body, and where rotation of the deflected sweep frame causes the cutting assembly to move in an arcuate path relative to an axis of a proximal end of the sweep frame, and a rotatable torque shaft extending through the catheter lumen and sweep frame and having a first end coupled to the rotatable cutter and a second end adapted to couple to a rotating mechanism.

As noted below, the sweep frame can have any number of configurations. However, the sweep frame shall allow for bending of the distal portion of the catheter as well as rotation of the distal portion of the catheter independently of the torque shaft and rotatable cutter. In some variations, the sweep frame rotates independently of the catheter body and in other variations, the sweep frame rotates with the catheter body. In other variations, a distal portion of the catheter body rotates with the sweep frame while a proximal portion of the catheter body remains stationary. In addition, devices of the present invention can have any number of sweep frames located about a length of the catheter body where each sweep frame allows bending of the associated segment of the catheter. These sweep frames can bend and be rotated independently of each other. Alternatively, bending or rotation of the sweep frames can be linked if so desired.

The systems of the present invention can further include a handle coupled to the proximal end, where the sweep frame is rotatable independently of the handle. Typically, the sweep frame is actuated by a sweep member or sweep shaft. The sweep shaft is fabricated such that it can translate axial force as well as rotational movement from the handle or proximal end of the device to the sweep frame.

In some variations, the sweep frame is configured to limit deflection of the cutting assembly to a pre-determined distance away from the axis of the proximal end of the sweep frame at a maximum angle of deflection. In additional variations, the bending stiffness and resulting potential apposition force can be varied with the deflection angle or displacement of the cutting assembly and with axial position along the sweep frame.

In additional variations, the weakened section of the sweep frame comprises a varying column strength that increases in a circumferential direction away from the first radial side to prevent radial twisting of the sweep frame when deflected. Such a configuration is intended to prevent twisting or torsion of the weakened section of the sweep frame upon bending. In one variation, the sweep frame comprises struts to accomplish such preferential bending towards the first radial side and increasing column strength away from the first radial side.

In most variations the sweep frame is located entirely within the catheter body. However, in additional variations, the sweep frame may be exposed or on an exterior of the catheter. In any case, the sweep frame is coupled to the catheter to permit bending and steering of the catheter.

The sweep frame structure described herein can be combined with any number of cutting assemblies as also described or as known to those skilled in the art.

For example, in a variation, the cutter can comprise a plurality of fluted cutting edges located on both a near fluted cutting portion and a far fluted cutting portion, where the near fluted cutting portion and the far fluted cutting portion are spaced along an axis of the cutter and the far fluted cutting portion has fewer fluted cutting edges than the near fluted cutting portion, where on rotation of the cutter the fluted cutting edges remove material from the body lumen.

The cutting assemblies can include a cutting housing having a plurality of openings along an exterior surface of the housing. Alternatively the housing can be a cylindrical housing having an open front face. Such an open faced housing can either rotate (either with the rotatable cutter or in an opposite direction) in which case the housing functions as a cutter. Alternatively, the open faced housing can remain stationary.

In additional variations of the device, the cutting assembly can include a dilator member extending distally from a front of the housing, the dilator member having a passage extending therethrough and being in fluid communication with the catheter lumen, where the dilator member comprises a tapered shape having a smaller diameter surface at a distal tip and a larger diameter surface adjacent to the front of the housing, such that as the dilator member advances through material, the dilator member dilates material away into the opening in the housing.

The present invention also includes methods for debulking occlusive material from within the body. Such methods may include advancing a catheter having an elongate member with a debulking assembly affixed to a distal end of the elongate member within the body lumen, positioning the debulking assembly adjacent to the occlusive material in the body lumen, the debulking assembly having a cutter and a bending frame coupled to a distal portion of the catheter and proximate to the debulking assembly, where the bending frame comprises at least a section having a reduced column strength on a first radial side of the bending frame, deflecting the bending frame in a direction of the first radial side by advancing a sweep member at the proximal end of the catheter, where deflecting the bending frame causes the debulking assembly to also deflect in the direction of the first radial side, rotating a torque shaft extending through the catheter and coupled to at least the cutter to debulk the occlusive material, and rotating the sweep member independently of the torque shaft to rotate the bending frame and cause the debulking assembly to sweep in an arcuate path relative to an axis of a proximal end of the bending frame.

As discussed herein, variations of the novel devices include one or more sweep frames and/or sweep tubes to cause deflection of the distal portion (and other portions) of the debulking device. The sweep frame improves conventional devices since it allows the catheter to stay straight when in the straight position. In other words, the sweep frame prevents the debulking catheter from developing an undesirable "bend" when the device is intended to be in a straight position. Such undesired set bends are common with conventional steerable catheters. Avoiding the undesirable set bend reduces the chance that the debulking device creates unwanted collateral damage to healthy tissue. For example, a conventional device that assumes a bend (either after multiple flexing, from an extended time in packaging, from exposure to heat) can come to rest against healthy tissue when the physician assumes that the device is straight. Clearly, activation of the conventional device in such a circumstance prevents the physician from limiting the debulking to the target tissue.

Aside from ease of construction (e.g., a simple and inexpensive construction) the sweep frame provides excellent column strength for improved forward cutting speed in straight and in deflected positions. This structure was found to prevent a failure mode where the sheath collapses onto and spiral wraps around a torque shaft. Moreover, the sweep frame provides excellent apposition force for better cutting at diameters larger than the catheter.

In addition, providing a sweep frame that must be compressed to deflect allows for selectively "tuning" the construction so that as the bending portion of the sweep frame reaches the desired maximum desired deflection, the segments forming the bending portion can mechanically interfere to prevent further bending.

In another variation, the sweep frames of the present devices can contain features so that a physician can determine the orientation of the bend of the device from a non-invasive imaging means. For example, the sweep frame or catheter coupled to the sweep frame can include one or more visualization mark(s) allowing for non-invasive determination of an orientation and direction of articulation of the sweep frame. The visualization mark can be shaped with asymmetry out of the bending plane that acts as a radiopaque marker (either a cutout or a protrusion) to show direction of device tip into/out of fluoroscopy plane when deflected. Marker could also be the addition of a stripe/band/wire etc of radiopaque material like tantalum, gold, platinum, etc.

In an additional variation to the method or device, the sweep member can be locked relative to the device to prevent the bending frame from further bending or unbending. It may also independently lock relative to the device to prevent sweep.

The devices and methods also include delivering fluid through a fluid port. The fluid may include a drug or other substance to aid in the procedure.

In another variation of a method for removing tissue within a body passage, the method can include advancing a catheter having debulking assembly affixed to a distal end of the catheter in the body, positioning the debulking assembly adjacent to the tissue in the body, applying a distal force at a proximal end of the catheter to deflect a bending frame coupled to distal portion of the catheter, rotating the bending frame while deflecting the bending frame to sweep the debulking assembly in an arcuate path relative to an axis of a proximal end of the bending frame, rotating a torque shaft extending through the catheter and coupled to at least the cutter to remove the tissue, and rotating the sweep shaft independently of the torque shaft to rotate the bending frame and cause the debulking assembly to sweep in an arcuate path relative to an axis of a proximal end of the bending frame.

Another variation of the method is to deflect the distal end and advance the catheter to cut in an axial direction. The axial cut pattern can be repeated at subsequent radial positions to remove tissue.

Another variation of the method is to position and deflect a second bending or sweep frame along the catheter body to advance the debulking assembly in the direction set by the first sweep frame to increase the reach of the debulking assembly. The second sweep frame can provide a reaction force to the apposition force of the cutter approximated against plaque or tissue without requiring a reaction force from the catheter body interacting with the vessel wall. The second bending frame can also be used to allow precise control of the cutter angle with respect to the tissue to be debulked. A second sweep shaft can be rotated to sweep the debulking assembly.

As discussed herein, some variations of the devices have the ability to articulate. This articulation allows for steering the device to the target site as well as creating a sweeping motion of tissue removal. This ability to steer can be useful when attempting to navigate a guidewire through tortuous anatomy. For example, a physician often encounters resistance when advancing a guidewire through tortuous anatomy, either due to occlusions within the vessel or the tortuous nature of the vasculature. When the physician encounters such resistance, the guidewire can be withdrawn within or slightly extending from a debulking catheter. The physician can then steer the debulking catheter to redirect the guidewire for advancement. Once the guidewire is in place, the physician can then activate the cutting mechanism to selectively remove tissue.

The devices described herein may have a cutter assembly having a portion of its housing having a curved surface and where the opening forms a plane across the curved surface such that as the cutting surface rotates across the opening, a portion of the cutting surface extends out of the housing through the opening. The cutter assembly may also have various other features as described below that improve the safety of the device as it is articulated while cutting. Furthermore the cutter may have a number of features to impel or drive cut tissue into the cutter assembly for eventual removal by one or more conveying members.

As noted, the devices described herein may have one or more conveying members that convey materials and/or fluids through the device. Such a feature is useful to remove cut tissue and debris from the site during the procedure. In some variations, the device may include multiple conveyors to deliver fluids and remove debris. However, the devices of the present invention may also have containers for use in capturing debris or other materials generated during the procedure.

Another feature for use with the inventions herein is the use of a grinding burr rotatably coupled to a tip of the device. The burr can be useful to remove tissue that is otherwise not conducive to cutting with the cutter assembly.

The devices described herein may use a guidewire for advancement through the body. In such cases the devices will have guide-wire lumens located within or about the catheter. Alternatively, a guide-wire section may be affixed to a portion of the device.

Devices of the present invention typically include a torque shaft to deliver rotational movement to components in the cutter assembly. The torque shaft may include one or more lumens. Alternatively, the torque shaft may be a solid or hollow member. Variations of the torque shaft also include those aspects known in catheter-type devices such as counter-wound coils, stiffening members, etc. In some variations, the torque shaft may have the conveying member integrally formed about the exterior or an interior surface of the shaft. Alternatively, or in combination, the conveying member may be placed on (or within) the torque shaft as described herein.

As noted herein, combinations of aspects of the devices, systems, and methods described herein may be combined as needed. Furthermore, combinations of the devices, systems and methods themselves are within the scope of the disclosure.

BRIEF DESCRIPTION OF THE DRAWINGS

FIG. 1A illustrates an exemplary variation of a device according to the present invention;

FIG. 1B shows an exploded view of the device of FIG. 1A;

FIGS. 12A, 12G, and 12B show a control system for rotating and articulating the cutter assembly;

FIG. 13 shows a device with a burr tip;

FIGS. 14A-14C provide examples of fluid delivery systems;

FIG. 15 shows the device placed within a stent or coil;

DESCRIPTION OF THE PREFERRED EMBODIMENT

Figure 1C:
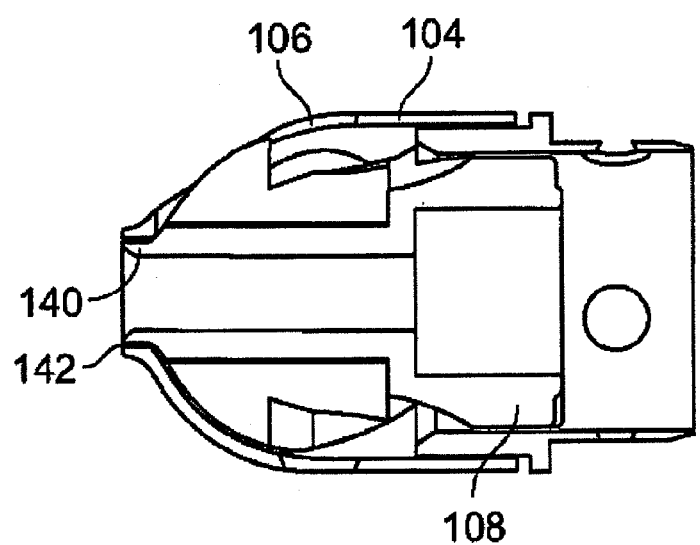
FIG. 1C shows a cross sectional view of the cutting assembly.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

FIG. 1A illustrates an exemplary variation of a device 100 according to the present invention. As shown the device 100 includes a cutter assembly 102 affixed to a catheter or catheter body 120. The catheter body 120 can be a reinforced sheath (e.g., a polymeric material with a braid). It is noted that the cutter assembly shown in the figures exemplary purposes only. The scope of this disclosure includes the combination of the various embodiments, or single elements of various embodiments, where possible, as well as the combination of certain aspects of the various embodiments.

FIG. 1A shows a variation of a tissue removal or debulking device 100 where the cutter assembly 102 is within the housing 104. In this variation, the cutter assembly contains a first set of cutting edges 112 and a second set of cutting edges 109, where the first cutting edges 112 extend along the entire length of the cutting assembly 102 (i.e., the entire length that is exposed in the openings 106 of the housing 104). In contrast, the second set of cutting edges 109 (in the figure only one such second cutting edge is visible) extend only along a portion. However, variations of the methods and devices described herein can include any number of cutter configurations as described herein or as known by those skilled in the art. Furthermore, although the illustrated device shows a plurality of openings 106 in the housing 104, alternative cutting assemblies can include a housing having a single opening on a distal face. Such open faced cutters are shown below.

FIG. 1A also shows the device 100 having a catheter body 120 extending from a distal portion 122 to a proximal portion (not shown). As discussed below, the catheter body 120 can be coupled to a rotating mechanism or motor 150 that ultimately drives the cutter assembly 102 via a torque shaft 114 as shown in FIG. 1B.

FIG. 1A further illustrates a variation of a sweep frame 250 located within the catheter body 250. Additional details regarding various sweep frames are provided below. In any case, the sweep frame 250 permits the distal portion 122 of the catheter 120 to bend or articulate in response to a distally directed force typically applied at a proximal portion of the catheter or at a handle of the device. For purposes of clarity, the sweep frame 250 is shown without the torque shaft 114 extending therethrough. However, the torque shaft shall extend through the sweep frame 250 to drive rotation of the rotatable cutter 108.

In the illustrated variation, the sweep frame 250 comprises a tube structure having a plurality of serrations, slots, or semi-circumferential openings 252. Overall, the area having the openings 252 on the sweep frame 250 weaken the frame 250 by providing a section of reduced column strength on a first radial side 254 of the sweep frame (i.e., the sides containing the openings). The portion 256 of the sweep frame 250 that is not weakened maintains a column strength that is greater than that of the first radial side 254 of the sweep frame 250. This constructions permits deflection of the distal portion of the device when an axial force is applied to the sweep frame 250 driving it against a fixed section (e.g., either the cutter assembly, a portion of the catheter body 120, etc.) As shown in FIG. 1B, this axial force compresses the sweep frame 250 causing the area with the weakened column strength to compress (i.e., the sides of the sweep frame 250 adjacent to the openings 252 move towards one another on the first radial side 254). This in turn causes the deflection of the spine or strengthened side 256 in a direction towards the first radial side 254. Because the sweep frame 250 is coupled to the catheter (either it is fully or partially encapsulated within the catheter body 120, the deflection of the sweep frame 250 causes deflection of the distal end of the catheter body and cutter assembly 102 in a direction towards the first radial side 254 causing an axis of the cutter assembly 102 to form an angle A with an axis of the proximal end 258 of the sweep frame 250.

The sweep frame 250 is rotatable independently of the rotatable cutter 108 and torque shaft 114. In certain variations, the sweep frame 250 is independently rotatable from the catheter body 120 as well. In such configurations, as the deflected sweep frame 250 rotates, the cutting assembly and/or distal catheter portion move in an arcuate path relative to an axis 260 of a proximal end 258 of the sweep frame 250. The of the sweep frame 250 can also be configured to rotate with the catheter body 120. In this latter configuration, the cutter assembly 102 can also rotate with the sweep frame 250 while the rotatable cutter 108 still is able to rotate independently of the sweep frame 250.

FIG. 1B also shows a variation of the cutting edges comprising a first set of cutting edges 112 that extend along (or substantially along) the cutter 108 and a second cutting edge 109 that extends only along a portion of the cutter 108. Although the number of cutting edges can vary, typically the cutting edges will be symmetric about an axis 111 of the cutter 108. For example, in one variation, the illustrated cutter 108 will have a pair of second cutting edges 109 symmetrically located about the cutter 108 and a pair of first cutting edges 112 symmetrically located about the axis 111 of the cutter 108. Accordingly, such a construction results in two cutting edges 112 located on a far or distal end of the cutter 108 and four cutting edges 109 and 112 located on a near or proximal end of the cutter 108.

Providing a cutter 108 with fewer cutting edges on a first cutting portion and an increased number of cutting edges on a second cutting portion, as shown, allows for a more aggressive cutting device. As illustrated in the figures, the cutter can be configured with cutting edges 109, 112 that are adjacent to grooves, channels, or flutes (where the combination is referred to as a "cutting flute"). The flute provides a path for the cut material to egress from the treatment site through the debulking device. By reducing the number of flutes on a far end of the cutter, the flutes can be made deeper. The deeper flutes allow the cutting edge adjacent to the flute to remove greater amounts of material. However, increasing the size of the material can also increase the chances that the material becomes stuck or moves slowly through the catheter during removal. To alleviate this potential problem and increase the efficiency of transporting the material through the catheter, the cutter can be configured with an increased number of cutting edges towards a rear of the cutter that reduce the size of the cut material.

FIG. 1B also shows the cutter coupled to a rotating mechanism 150. In this variation the rotating mechanism couples to the cutter via a torque shaft 114 that transmits rotational energy from the rotating mechanism 150 (e.g., an electric, pneumatic, fluid, gas, or other motor) to the cutter 108. Variations of the devices include use of a rotating mechanism 150 located entirely within the body of the device 100. In one variation, the rotating mechanism 150 may be outside of the surgical field (i.e., in a non-sterile zone) while a portion of the device (e.g., the torque shaft—not shown) extends outside of the surgical field and couples to the rotating mechanism. The rotating mechanism can be a motor drive unit. In one working example, a motor drive unit having 4.5V and capable of producing cutting speeds up to 25K rpm was used. Another example of a motor drive unit included supplying the motor at 6V nominal, running at about 12,000 RPM with higher torque. This was accomplished by changing the gear ratio from 3:1 to 1:1.

The device 100 may also include a vacuum source or pump 152 to assist in evacuation of debris created by operation of the device. Any number of pumps or vacuum sources may be used in combination with the device. For example, a peristaltic pump may be used to drive materials from the device and into a waste container. FIG. 1B also shows the device 100 coupled to a fluid source 154. As with the rotating mechanism, the vacuum source and/or fluid source may be coupled to the device from outside the surgical field.

It may be advantageous to rotatably couple the torque shaft to the drive unit electromagnetically, without physical contact. For example, the torque shaft 114 can have magnetic poles installed at the proximal end, within a tubular structure that is attached to the sheath around the torque shaft. The stationary portion of the motor can be built into a handle that surrounds the tubular structure. This allows the continuous aspiration through the sheath without the use of high speed rotating seals.

The device may also include a ferrule 116, as shown in FIG. 1B, that permits coupling of the catheter body 120 to the cutter assembly 102. The ferrule 116 may serve as a bearing surface for rotation of the cutter 108 within the cutter assembly 102. In the illustrated variation, the torque shaft 114 rotates inside the outer catheter body 120, sweep frame 250 and ferrule 116 to rotate the cutter and pull or aspirate tissue debris in a proximal direction. The clearance between the catheter tube and conveying member 118, as well as the pitch and thread depth of the conveying member 118, are chosen to provide the desired pumping effectiveness.

In one variation of the device, the housing 104 is connected to the catheter body 120 via the ferrule 116 and thus is static. The cutter 108 rotates relative to the housing 104 such that the cutting surface 112 on the cutter 108 shears or cleaves tissue and trap the tissue inside the housing 104 so that it can be evacuated in a proximal direction using the impeller action of the helical flutes and vacuum from the torque shaft. In alternate variations, such as where the housing includes a forward cutting surface, the housing 104 rotates as well as the cutter. Accordingly, the ferrule can serve as a bearing surface for both the housing and cutter.

The ferrule 116 can have a distal bearing surface to bear against the proximal surface of the cutter 108 and keeps the cutter axially stable in the housing 104. In cases where the housing is stationary, the ferrule 116 can be rigidly bonded/linked to the housing 104 using solder, brazing, welding, adhesives (epoxy), swaging, crimped, press-fit, screwed on, snap-locked or otherwise affixed. As shown, the ferrule 116 can have holes or other rough features that allow for joining with the catheter body. While adhesives and heat fusing may be employed in the construction, such features are not required. Often adhesives are unreliable for a small surface contact and heat fusing can cause the tube to degrade. The use of a mechanical locking ring 126 allows the cutting assembly 102 to be short. Such a feature is important for maximizing the flexibility of the distal section of the catheter as it is required to navigate tortuosity in blood vessels. In one variation, a ring or band (126) can be swaged onto the catheter body 120 and over the ferrule 116. This drives portions of the ring/band as well as the catheter body into the openings of the ferrule allowing for increased strength between the cutter assembly 102 and catheter body 120.

As shown in FIG. 1C, in certain variations, the housing 104 can have a distal nose with a center lumen 142 for receiving a mating piece 140 of the cutter 108. Such features assist in centering the cutter 104 concentrically inside the housing 104. As noted below, variations of the devices include the addition of a burr element (as shown below) for grinding hard tissue such as calcified plaque or a dilator member for separating materials towards the openings 106.

The geometry of the cutter 108 and housing 104 can be used to tailor the desired degree of cutting. The housing 104 and orientation of the openings 106 can be used to limit the depth of cutting by the cutter 108. In addition, the distal end of the housing 104 may be domed shaped while the proximal end may have a cylindrical or other shape. For example, by creating larger windows 106 in the housing a larger portion of cutter 108 may be exposed and the rate of cutting increased (for a given rotation speed). By placing the cutting window 106 on a convex portion or side wall of the housing, the debulking effectiveness is much less sensitive to the alignment of the cutter housing to the lesion, than if the window were on the cylindrical portion of the housing. This is a key performance limitation of traditional directional atherectomy catheters. In addition, placement of the window on the convex portion of the housing creates a secant effect (as described below).

Figure 1D:
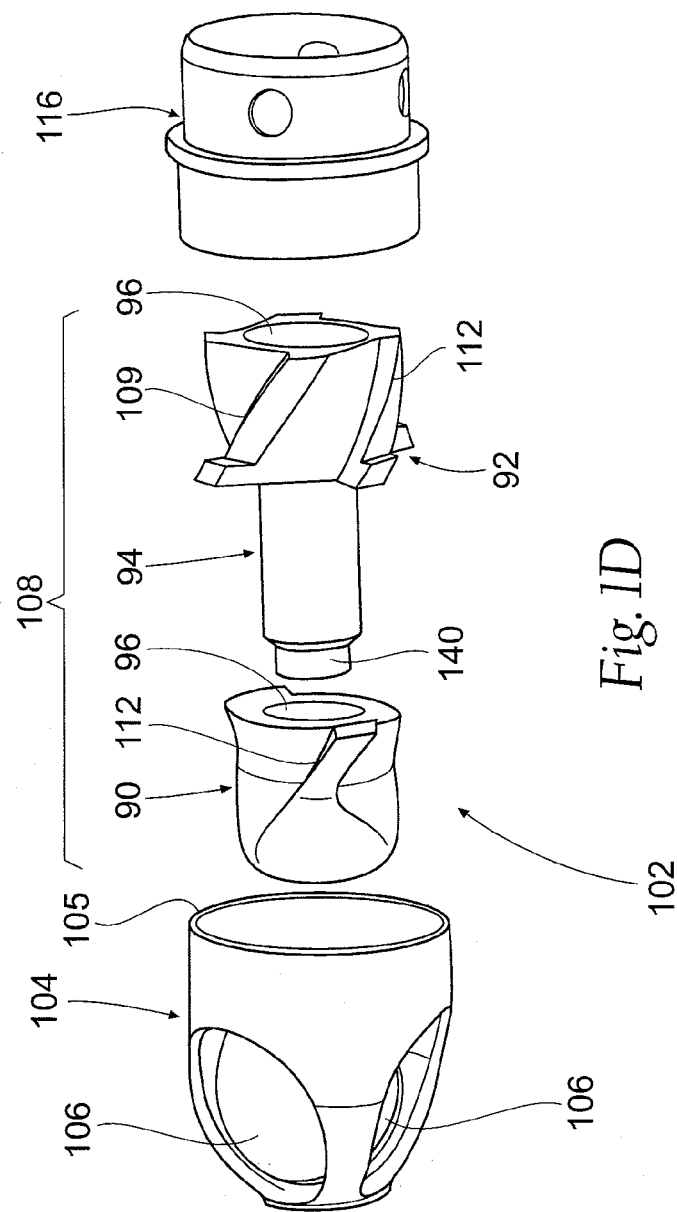
FIG. 1D shows an exploded view of the cutting assembly of FIG. 1A.

FIG. 1D illustrates an exploded view of a cutter assembly 102 and ferrule 116. In this variation, the cutter assembly 102 includes a housing 104 having three openings 106 symmetrically placed about a sidewall 105 of the housing. FIG. 1D also shows a variation of cutter 108 that comprises a far or distal portion 90 mounted on near or proximal portion 92 (where the near cutter portion can also be referred to as a cutter core adapter). The near cutter portion 92 contains a shaft 94 terminating in a mating piece 140 for coupling the cutter 108 to the housing 104 (where the mating piece 140 nests within an opening in a front face of the housing 104. The cutter 108 can also include a passage 96 to allow for passing of a guidewire through the device.

Although the inventive device includes cutters formed from in a unitary body, providing the cutter 108 with far and near 90, 92 cutter portions allows for optimal selection of materials. In addition, as shown, a first cutting edge 112 can extend along both cutter portions 90, 92 while a secondary cutting edge 109 extends only along the near cutter portion 92. Given this configuration, when the cutter portions 90, 92 join to form the cutter 108 the far portion 90 of the cutter only contains two fluted cutting edges while the near cutting portion 92 includes four fluted cutting edges. Naturally, any number of fluted cutting portions are within the scope of the invention. However, variations include fewer cutting edges on a distal end of the cutter relative to the number of cutting edges on a proximal end of the cutter. Moreover, the cutting edges may or may not be symmetrically located about the cutter.

FIGS. 2A-6H illustrated below show various examples of cutting assemblies that can be incorporated with the steerable tissue removal catheters employing a sweep frame.

Figure 2A:
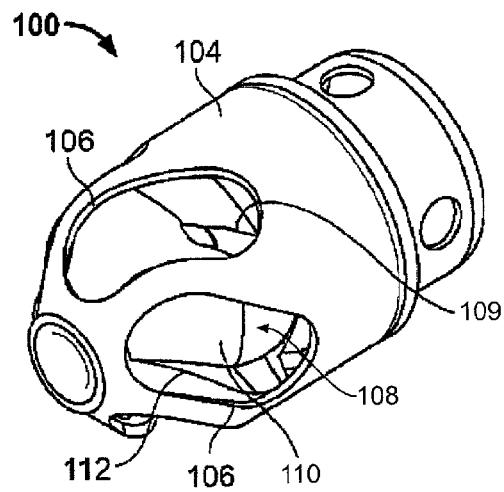
FIG. 2A shows the cutting edges through openings of a housing.

FIG. 2A illustrates the cutting assembly shown in FIGS. 1A through 1D where the openings 106 form helical slots in the housing 104. The openings 106 may or may not be aligned with the cutting edges 109, 112 of the cutter 108. For aggressive cutting, the slots 106 and cutting edges 109, 112 can be aligned to maximize exposure of the tissue to cutting edges. In other words, the cutting edges 109, 112 and openings 106 can be in alignment so all cutting edges 109, 112 are exposed at the same time to allow simultaneous cutting. Alternatively, alignment of the openings and edges 109, 112 may be configured so that fewer than all the cutting edges 109, 112 are exposed at the same time. For example, the alignment may be such that when one cutting edge is exposed by an opening 106, the remaining cutting edges are shielded within the housing 104. Variations of such a configuration allow for any number of cutting edges to be exposed at any given time. In addition, the variation depicted in FIG. 2A shows a window or opening 106 large enough to expose both the first 112 and second 109 cutting edges. However, in alternate variations, the windows can be configured to only expose the cutting edges 112 on the far end of the cutter 108.

In another variation, to even out the torque profile of the device when cutting, the cutter 108 can be configured such that the number edges/cutting surfaces 109, 112 of the flutes 110 that are aligned with the housing openings 106 does not vary throughout the rotational cycle. This prevents the catheter from being overloaded with torque spikes and cyclic torque variations due to multiple cutting edges/flutes engaging with tissue in synchrony. In other words, the length of the cutting surface 112 exposed through the openings 106 of the housing 104 remains the same or constant.

Figure 2B:
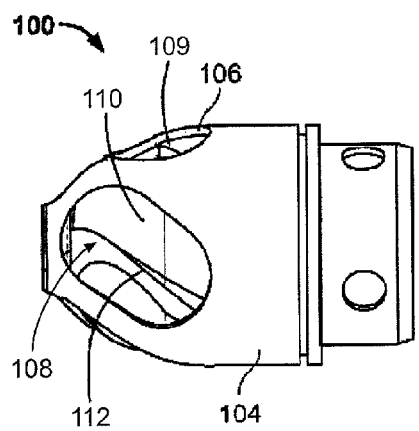
FIG. 2B shows a side view of the cutting assembly.

In the variation shown in FIG. 2B, the cutting edges 109, 112 are configured to capture debris within the flute 110 as the cutter 108 rotates. Typically, the cutter 108 may be designed with a secant effect. This effect allows for a positive tissue engagement by the cutter 108. As the cutter 108 rotates through the opening, the cutting edge moves through an arc, where at the peak of the arc the cutting edge slightly protrudes above a plane of the opening. The amount of positive tissue engagement can be controlled through selection of the protrusion distance through appropriate design of the housing geometry (for example, by a combination of location and size of the window and radius of curvature of the housing). The cutting edge 109 or 112 can extend out of the housing 104 through the window 106 as it rotates. This structure can also be designed to drive or impel the debris to the conveying member 118. In this case, the flutes 110 within the cutter 108 are helically slotted to remain in fluid communication with the conveying member 118. Variations of the device 100 can also include a vacuum source 152 fluidly coupled to the conveying member 118. In order to improve the impelling force generated by the cutters, variations of the cutter have helical flutes 110 and sharp cutting edges 112 that are parallel to each other and are wound from proximal to distal in the same sense as the rotation of the cutter. When the cutter rotates, it becomes an impeller causing tissue debris to move proximally for evacuation.

Figure 2C:
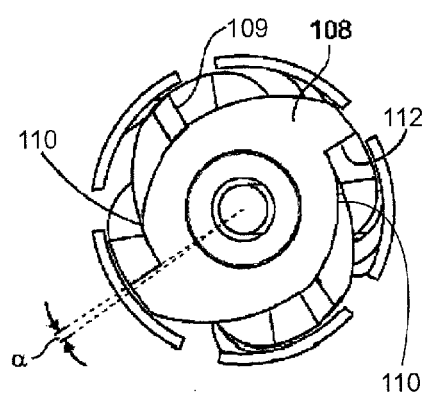
FIG. 2C illustrates a positive rake angle.

As shown in FIG. 2C, variations of the device may have cutting edges 109, 112 with positive rake angles α—that is the cutting edge is pointed in the same direction as that of the cutter rotation. This configuration maximizes the effectiveness of the impelling and cutting action (by biting into tissue and avoiding tissue deflection). The cutter, as described above, is preferably made of hard, wear-resistant material such as hardened tool or stainless steels, Tungsten carbide, cobalt chromium, or titanium alloys with or without wear resistant coatings, such as Titanium Nitride. However, any material commonly used for similar surgical applications may be employed for the cutter. The outer surfaces of the proximal end of the cutter 108 are typically blunt and are designed to bear against the housing 104. Typically, these surfaces should be parallel to the inner surface of the housing.

FIGS. 2A-2B also show a surface of the cutter 108 having a curved-in profile distally and is close to the housing 104 surface. Note that housing openings 106 with this curved profile allows the cutting edge 112 to protrude beyond the housing's outer surface. In other words, the openings 106 form a secant on the curved surface of the housing 104. Such a feature allows improved cutting of harder/stiffer material like calcified or stiff fibrous tissue where such tissue does not protrude into the housing 104.

By controlling the number of cutting edges 109, 112 that are exposed through openings 106 in the housing 104, it is possible to control the relative amount of cutting engagement (both length of cutting and depth of cut, together which control the volume of tissue removed per unit rotation of the cutter). These features allow independent control of the maximum torque load imposed on the device 100. By carefully selecting the geometry of the flutes and or cutting edges 112 relative to the openings 106 in the housing, it is possible to further control the balance of torque. For example, the torque load imposed on the device is caused by the shearing of tissue when the cutter edge is exposed by passing through the housing window. If all cutter edges simultaneously shear, as for example when the number of housing windows is an even multiple of cutter edges, the torque varies cyclically with rotation of the cutter. By adjusting the number of cutters and windows so one is not an even multiple of the other (for example, by using 5 windows on the housing and 4 cutting edges on the cutter), it is possible to have a more uniform torque (tissue removal from shearing action) during each cycle of the cutter.

Figure 3A:
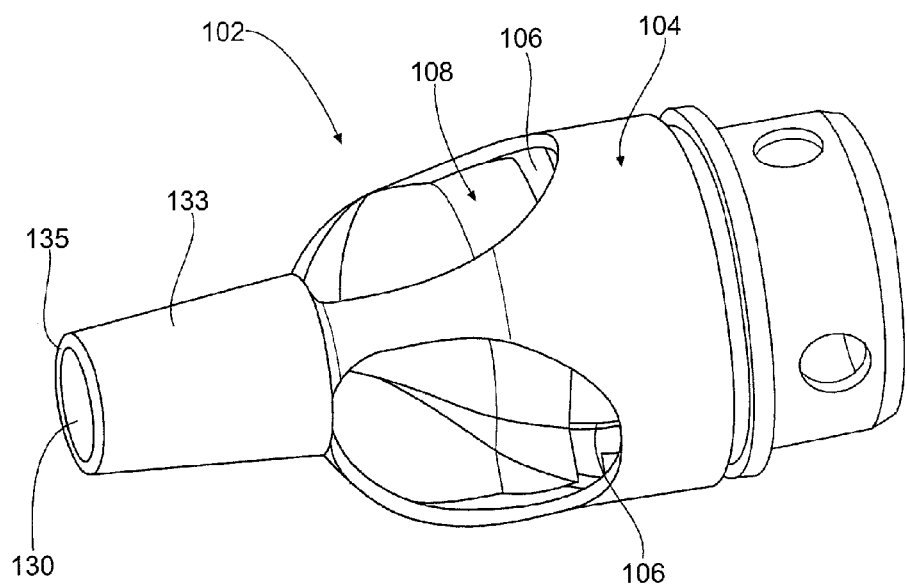
FIG. 3A illustrates a variation having a dilation member.

FIG. 3A shows a variation of a cutter assembly 102 where a housing 104 of the assembly 102 includes a conical, tapered, or dilator extension 133 extending from a front face of the housing 104. The dilator extension 133 serves a number of purposes namely that it can keep the cutting assembly 102 from damaging a vessel wall. In addition, the added structural reinforcement of the front face of the housing 104 reduces the chance that the rotating cutter 108 actually cuts through the housing 104 if the struts were to deflect inward. However, one important feature of the dilator extension 133 is that it provides a tapered surface from a guidewire to the openings 106 in the housing 104. Accordingly, as the dilator extension 133 advances through occlusive material, the dilator extension 133 forces or dilates material away from a guidewire towards the openings 106 and cutting edges. In order to dilate material away from a center of the device, the dilator extension 133 must have sufficient radial strength. In one example, the dilator extension 133 and housing 104 can be fabricated from a single piece of material as discussed herein.

The dilator extension 133 typically includes an opening 130 for passage of a guidewire. In addition, in most variations, a front end 135 of the dilator extension 133 will be rounded to assist in moving the occlusive material over a surface of the dilator 133. Furthermore, the surface of the dilator extension 133 can be smooth to permit sweeping of the cutting assembly 102 as discussed below. Alternatively, the dilator extension 133 can have a number of longitudinal grooves to direct material into the openings 106. In additional variations, the dilator extension 133 may not include an opening 130. In such a case, the dilator extension 133 would fully taper to a closed tip.

Figure 3B:
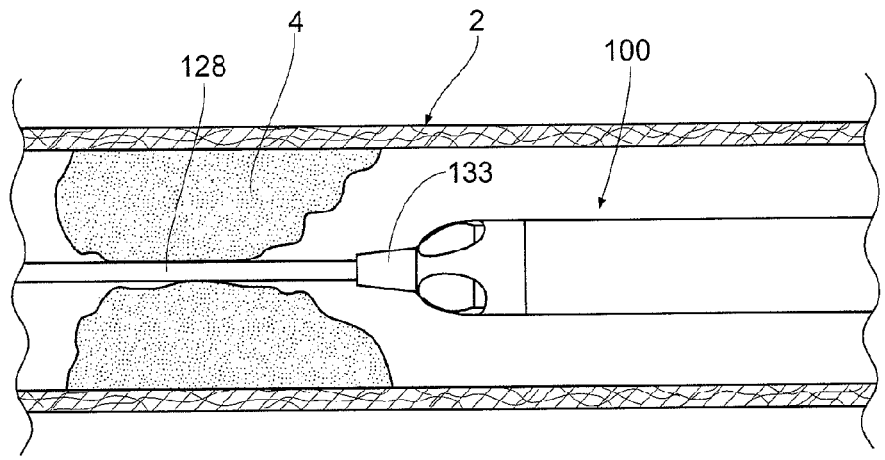
FIGS. 3B-3D show conceptually the use of a debulking device having a dilating member.
Figure 3C:
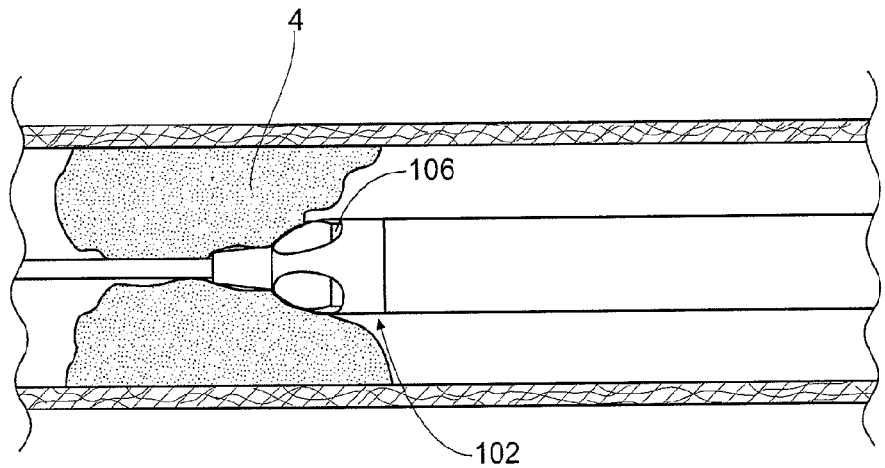
Figure 3D:
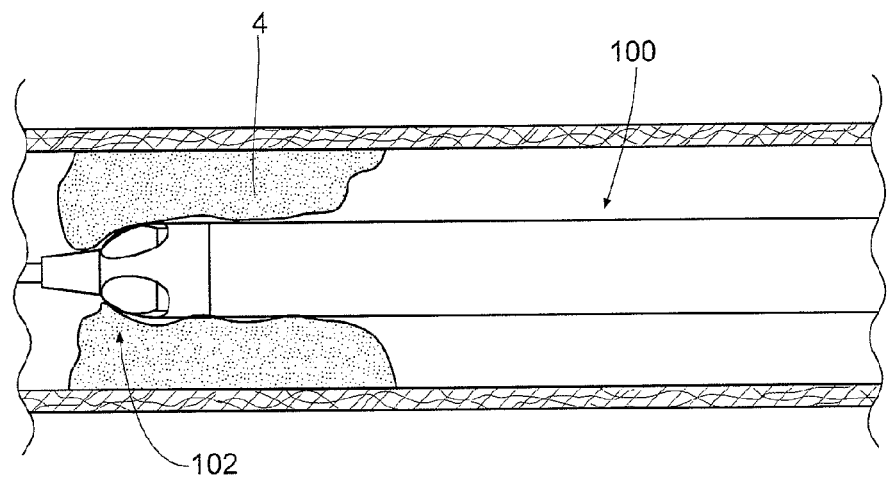

FIGS. 3B to 3D conceptually illustrate use of a debulking device having a dilating member 133. In this variation, the device 100 is advanced over a guidewire 128. However, use of a guidewire 128 is optional. As the device 100 approaches the plaque or occlusive material 4, the dilating member 133 forces the plaque 4 away from a center of the debulking device 100 and towards openings 106 in the cutting assembly 102 as shown in FIG. 3C. Clearly, the dilating member 133 must have sufficiently radial strength so that it forces the obstruction towards the openings 106. However, in those variations where the dilating member 133 is conical or tapered, the plaque material 4 is gradually moved towards the openings 106. In those devices not having a dilating member 133, the physician must apply excessive force to move the cutter against the plaque 4. In some excessive cases, the cutter actually shears through the housing leading to failure of the device. FIG. 3D illustrates a situation where the debulking device 100 traverses the entire occlusion 4. However, as noted below, the device may be configured for sweeping within the vessel. As such, the physician may choose to sweep the device 100 within the occlusion to open the occlusion during traversal of the occlusion or after a path is created through the occlusion. In either case, the nature of the dilation member 133 also functions to keep the cutting assembly 102 spaced apart from a wall of the vessel 2.

Figure 4A:
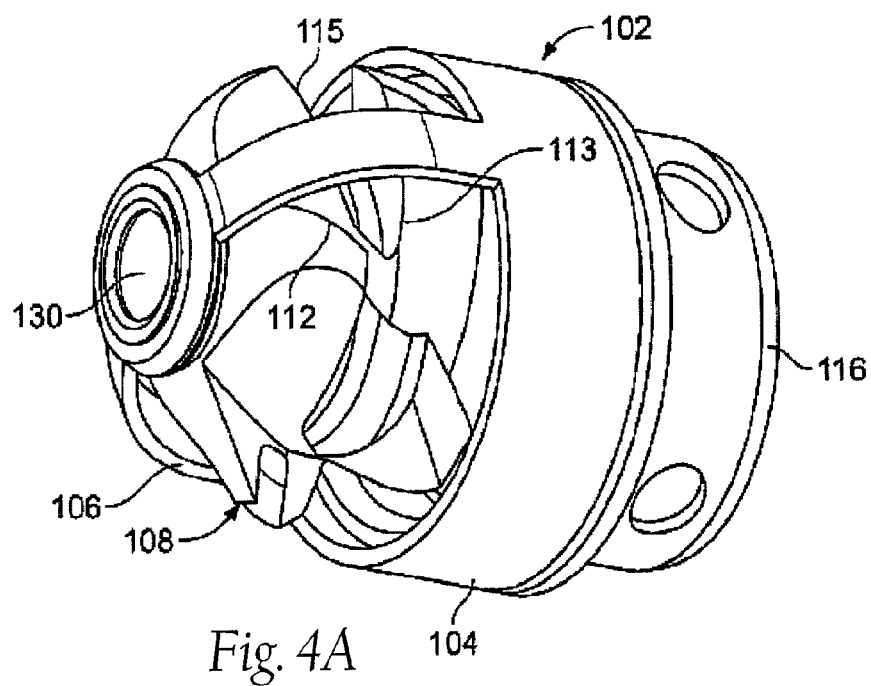
FIGS. 4A-4B show a variation of a shielded cutter having a plurality of front cutting surfaces, rear cutting surfaces, and fluted cutting surfaces.
Figure 4B:
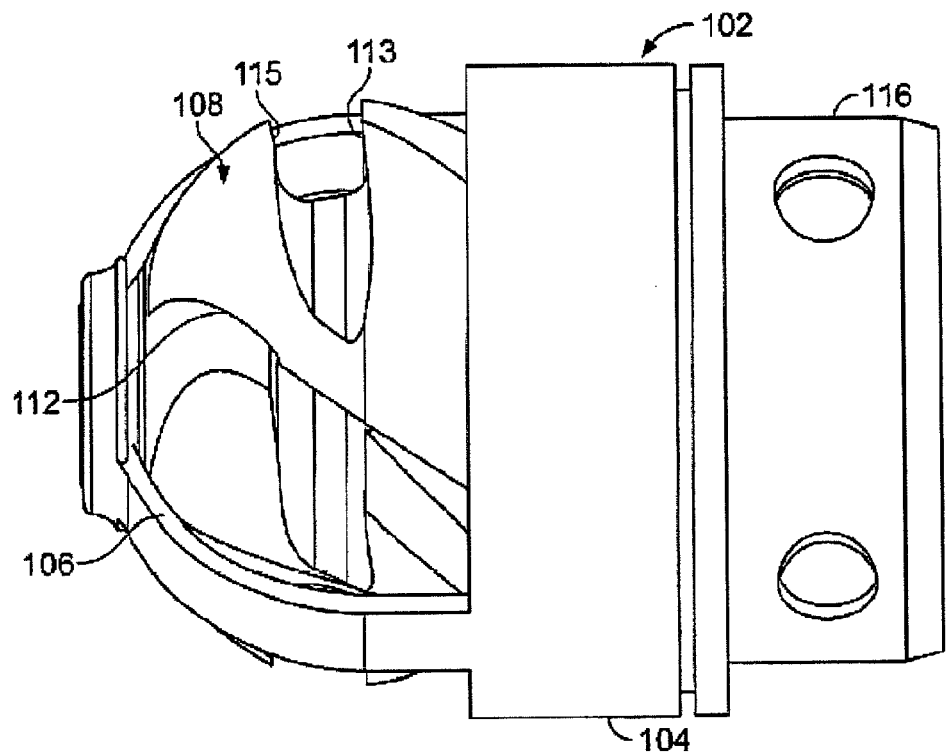

FIGS. 4A and 4B show an additional variation of a cutting assembly 102 for use with various debulking devices. FIG. 4B shows a side view of the cutter assembly 102 of FIG. 4A. In this example, the cutting assembly 102 includes larger windows 106 to accommodate a cutter 108 that includes a plurality of directional cutting surfaces 112, 113, 115. As the cutter 108 rotates within the housing 104, the fluted cutting edge 112 cuts in a direction that is tangential to a rotational direction of the cutter 108. In other words, the fluted cutting edges 112 cut material that is about the perimeter of the cutter 108 as it spins. The cutter 108 also includes on or more forward and rearward cutting surfaces 113, 115. These cutting surfaces 113, 115 engage tissue when the catheter is run in a forward direction or rearward direction. The ability to engage and remove engagements in the multiple directions have been shown to be important for effective debulking. However, a variation of a cutter 108 in the present invention can include a cutter 108 with one or two directional cutting surfaces. For example, the fluted cutting edges 112 can be combined with either the forward 113 or rearward 115 cutting surfaces. The ability to debulk in a forward, rearward and rotational directions also reduces the chance that the cutter assembly deflects from stubborn or hard tissue.

Figure 5A:
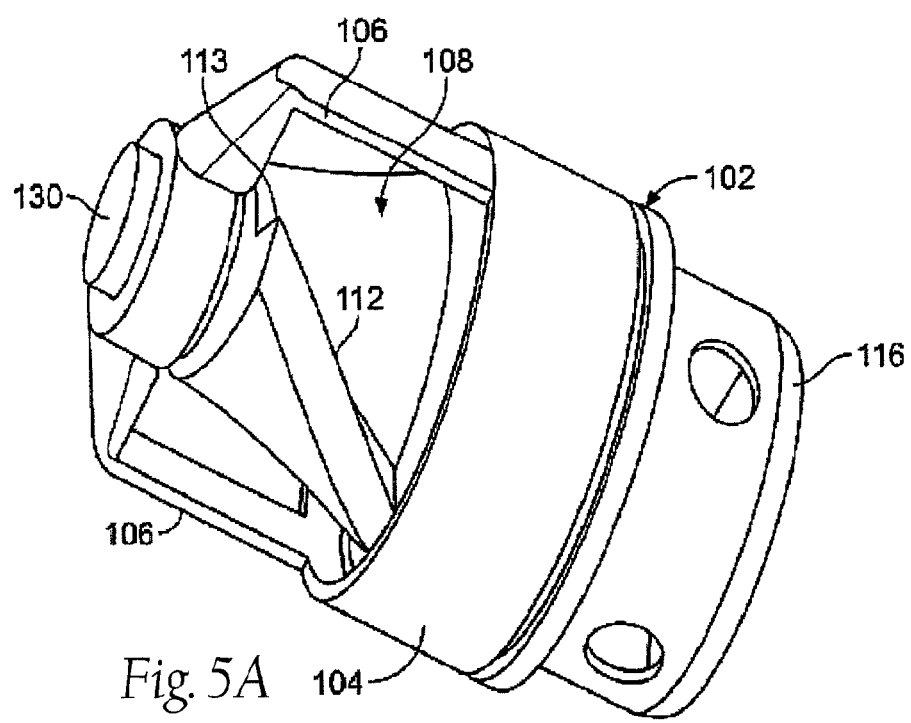
FIGS. 5A-5B show another shielded cutter having a plurality of front cutting surfaces and fluted cutting surfaces.
Figure 5B:
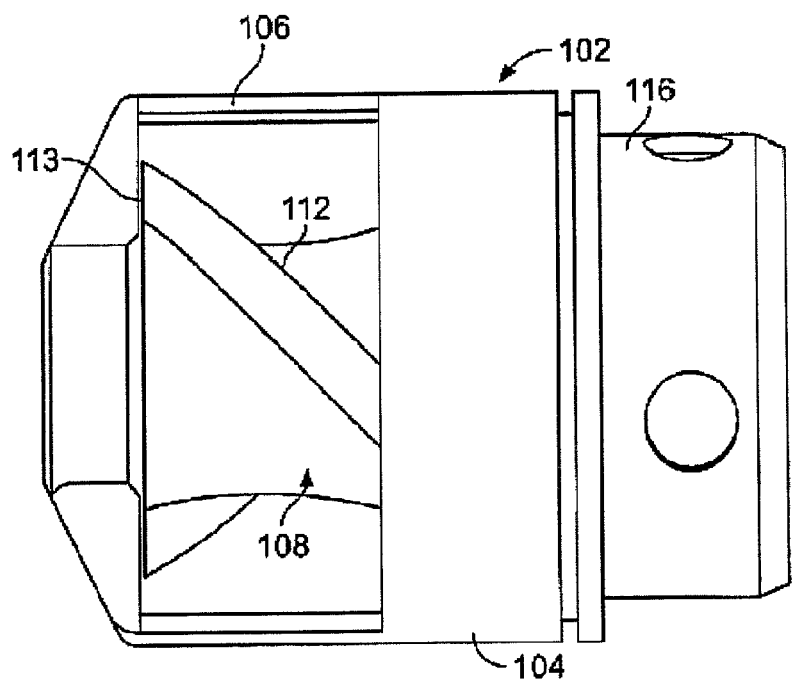

FIGS. 5A and 5B show another variation of a cutter assembly 102 having a forward cutting surface 113 on a front of the cutter 108. In this variation, the cutter housing 104 includes two large openings 106 that allow the forward cutting surface 113 to engage tissue when moved in a distal direction. The cutter 108 also includes a plurality of fluted cutting edges 112.

Figure 6A:
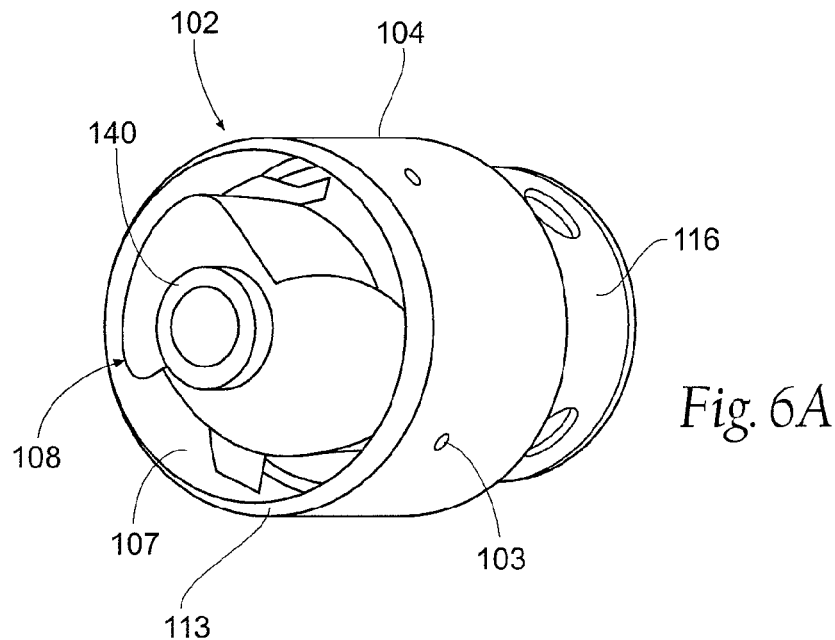
FIGS. 6A-6D show a cutter assembly having an open ended housing.
Figure 6B:
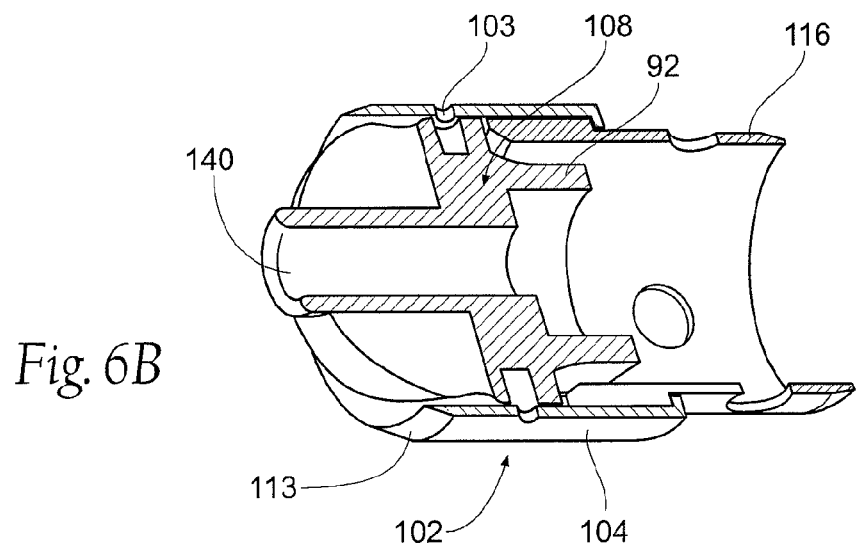
Figure 6C:
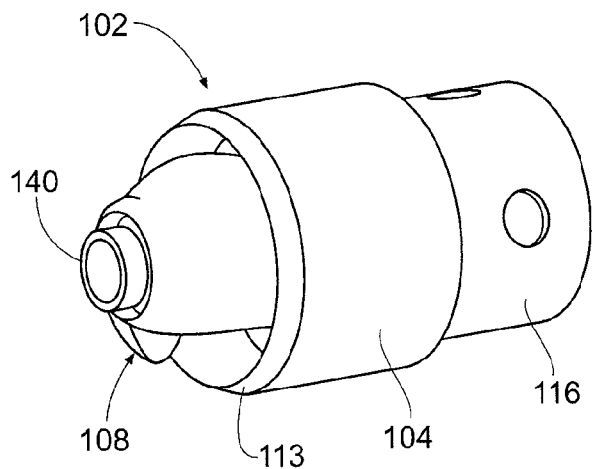

FIGS. 6A and 6C illustrates another variation of cutter assemblies 102 where the housing 104 includes an opening 107 located on a front face of a cylindrical housing 104. The cylindrical housing 104 containing a cutter 108 therein. In such a variation, the front edge of the housing 104 can function as a front or forward cutting surface. As shown, the front cutting surface 113 can be beveled on an outside surface of the housing 104. Such a beveled feature reduces the risk of the cutting surface 113 from gouging or otherwise damaging the wall of a vessel. As noted above, the forward cutting surface 113 engages and removes tissue or plaque 4 when the device is advanced in a distal direction within a body lumen 2 as shown in below. As discussed herein (see FIG. 11A), features of the device, including a guidewire 128 assist in preventing the device from excessively cutting the lumen wall 2.

The cutter 108 construction can be similar to that shown above. Namely, where the cutter has a varying number of cutting edges on different portions. Alternatively, the cutter 108 can be a conventional fluted cutter. In one variation, the cutter 108 will be tapered or rounded such that the front of the cutter comprises a rounded or partial-ball shape.

The housing 104 can either be configured to rotate with the cutter 108 or can be stationary and function as a scraping, scooping, or chisel type surface. For example, FIGS. 6A and 6B show a variation where the housing 104 can be affixed to the cutter 108 allowing for rotation of the entire cutting assembly 102 about the catheter body (not shown) or ferrule 116. In the illustrated example, the cutting assembly 102 includes adjoining recessed pin cavities 103 for securing the housing 104 to the cutter 108. FIG. 6B shows a cross sectional view of the cutter assembly 102 of FIG. 6A. As illustrated, in this particular variation, the entire cutting assembly 102 rotates relative to the ferrule 116 which provides a bearing surface for the rotational housing 108. The proximal or near portion 92 of the cutter 108 rotates within the ferrule while the proximal end of the housing 104 rotates about the ferrule 116.

The housing 104 can be linked to the cutter 108 in a variety of ways as is well understood by those skilled in the art. For example the housing 104 can be directly linked or affixed to the cutter 108 via connection points 103 so that both rotate together. Alternatively, the housing 104 can be geared to rotate faster or slower than the cutter 108. In yet another variation, the gearing can be chosen to permit the housing 104 to rotate in an opposite direction than the cutter 108.

Variations of the cutting assemblies include cutters 108 that protrude partially from the forward cutting surface 113 of the housing 104. In other variations, the cutter 108 can extend further from the housing 104 or the assemblies can comprise cutters 108 that are totally recessed within the housing 108. In certain variations, it was identified that aligning the cutting surface 113 of the housing 104 with the deepest part of the flute on the cutter 108 allows for improved clearing of debris, especially where a single or double fluted cutting edge configuration is used on a distal portion of the cutter.

In any case, the fluted cutting edge 112 impels tissue debris back into the catheter. The outer diameter of the housing, proximal to the forward cutting surface 113 can be smooth to protect the lumen wall from the cutting action of the cutting edges. When the cutting assembly 102 is deflected, the outer diameter of the housing 102 becomes flush against the lumen wall and prevents the cutting edges from engaging the vessel wall. As the cutter assembly is advanced forward, it removes plaque 4 protruding from the lumen 2 wall and tissue debris is impelled backwards by the fluted edge 112 of the cutter 108.

Figure 6D:
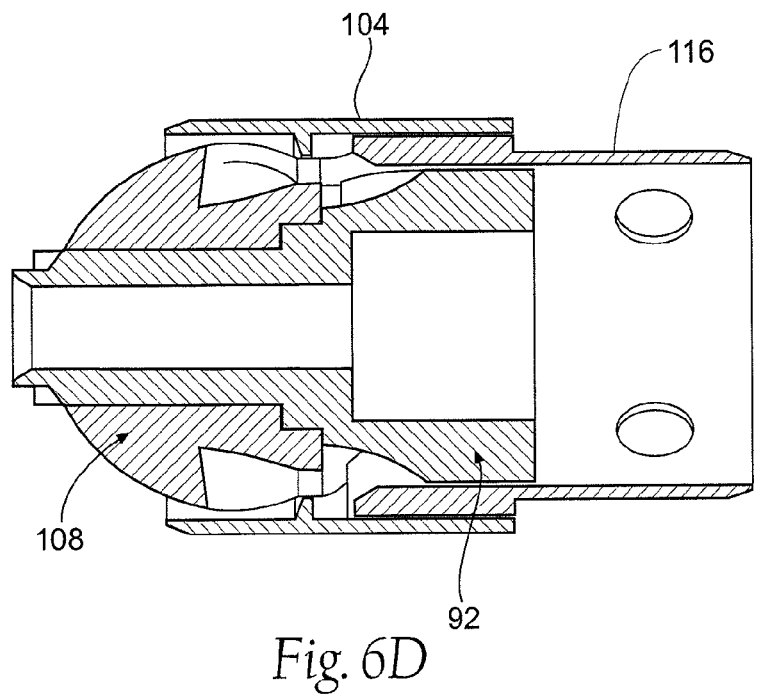

FIGS. 6C and 6D illustrate a variation of a cutting assembly 102 where a housing 104 of the cutting assembly 102 remains stationary about a catheter body (not shown) or ferrule 116 while the cutter 108 rotates within the ferrule.

FIG. 6D illustrates a partial cross sectional view of the cutting assembly 102 of FIG. 6C where the inner portion of the ferrule 116 provides a bearing surface for the proximal end 92 of the cutter 108. The housing 104 is affixed to the ferrule 116 and may also function as a bearing surface for the rotating cutter 108.

Figure 6E:
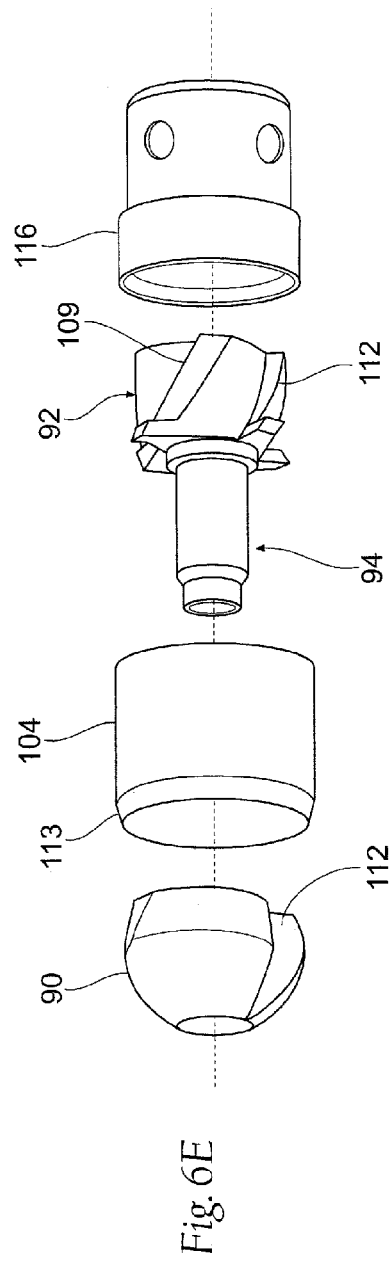
FIG. 6E shows an exploded view of the cutter assembly of FIG. 6C.

FIG. 6E shows an exploded view of the cutting assembly of FIG. 6C. Again, the cutter 108 can include a distal or far cutting portion 90 and a proximal or near cutting portion 92. The illustrated configuration provides a device having fewer cutting edges 112 on a distal portion 90 of the cutter and increased cutting edges 109 and 112 on a proximal cutting portion 92. However, variations include a traditional fluted cutter as well. The housing 104 is mounted about the cutter portions 90 and 92 and optionally secured to either the catheter body (not shown) or ferrule 116. As noted above, the housing 104 can also be affixed to the cutter so that it rotates with the cutter.

In alternate variations, the cutter assembly 102 the mating surface 140 can function as a blunt bumper at the very tip of the cutter 108 that acts as a buffer to prevent accidental cutting into the guidewire or the vessel wall given the cutter assemblies' open distal design. In additional variations, the housing 104 could be expandable (such as a basket or mesh). As the cutter 108 gyrates inside the housing, the housing expands to cut a larger diameter.

Figure 6F:
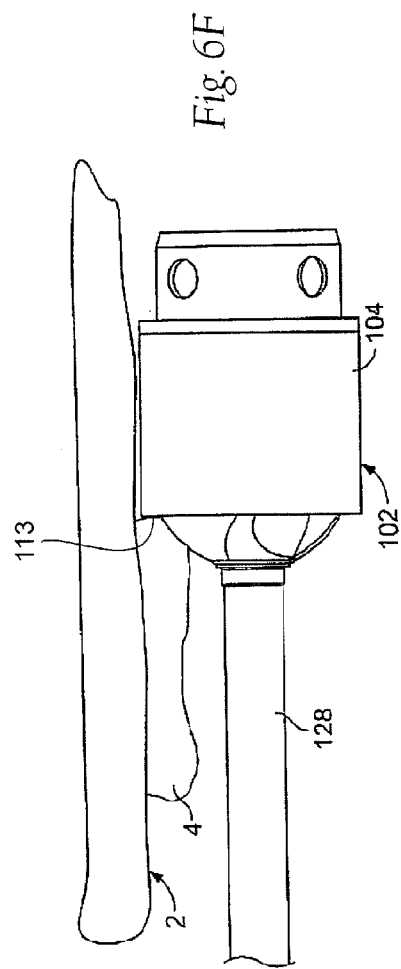
FIG. 6F shows a cutter assembly with the open ended housing removing material from a lumen wall.
Figure 6G:
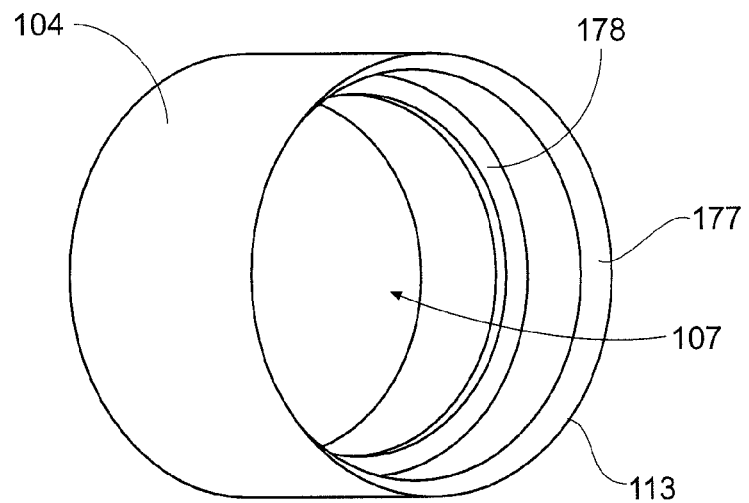
FIGS. 6G-6H shows a respective perspective and cross sectional side view of a variation of an open ended cutter housing with an inner bevel.

FIG. 6F illustrates a cutting assembly 102 having a forward cutting surface 113 at a distal opening 117 of a housing 104. The housing 104 rotates along with the cutter 108 to assist in removal of tissue. As noted above, the forward cutting surface 113 engages and removes tissue or plaque 4 when the device is advanced in a distal direction within a body lumen 2 as shown in FIG. 5E. As discussed below, features of the device, including a guidewire 128 assist in preventing the device from excessively cutting the lumen wall 2.

Figure 6H:
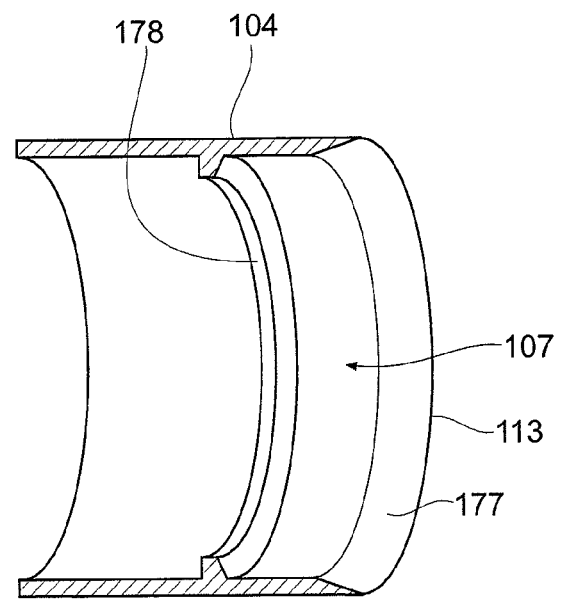

FIGS. 6H and 6I show a respective perspective view and cross-sectional side view of another variation of an open ended cutter housing 104. As shown, the cutter housing 104 includes an opening 107 located on a front face of a cylindrical housing 104. In this variation, the front edge of the housing 104 can function as a front or forward cutting surface and has a beveled surface 177 on an inside surface of the housing 104. Such a beveled feature reduces the risk of the cutting surface 113 from driving into the wall of a vessel. As shown, some variations of the cutter housing 104 include a bearing surface 178 located within the housing 104. In an additional variation, to control the degree to which the cutting assembly removes tissue, the distal end or cutting surface 177 of the housing 104 can be scalloped or serrated. For example, instead of being uniform, the cutting surface 177 can vary along a circumference of the housing in an axial direction (e.g., the serrated edges of the cutter extend along an axial length of the housing).

The tissue debulking catheters described herein can perform biopsies, tumor removal, fibroid treatment, debulking of unwanted hyperplastic tissues such as enlarged prostate tissue, or other unwanted tissue such as herniated spinal disc material. The flexible, low profile catheter allows for ease of access to the treatment site and minimizes trauma or collateral damage to surrounding healthy tissue. With the continuous aspiration capability, contamination of the surrounding tissue during device introduction, treatment and removal is reduced or even eliminated. In addition, aspiration can be used to transfer biopsy tissue samples to outside the body for testing with the catheter remains in situ. This helps the physician make real time decision in advancing treatment of malignant tissue. The shield on the cutter assembly maintains controlled excision of tissue by limiting the depth of cutter engagement and thereby prevents the physician from inadvertently cutting into healthy surrounding tissue. The tip steering capability of the cutter allows the physician to direct the cutter towards desired site of tissue removal and minimizing collateral tissue damage. Finally, by deflecting the cutter and rotating the deflection to sweep in an arc, the catheter can excise large tumors or tissue lumps larger than the diameter of the catheter. Thus, excision of large tumors can be achieved through a small access channel and thereby minimizing trauma to the patient.

The construction of the cutting assembly can provide for additional modes of energy delivery. For example, the catheter excises tissue in vascularized regions excessive bleeding can occur (e.g., lung biopsy and excision). Accordingly, energy can be delivered to the target site via a conductive cutter assembly (i.e. shield or even cutter). Sound energy (ultrasound), electrical energy (radio frequency current), or even microwaves can be used for this purpose. These energy sources delivered through the cutter can also be used to denature tissue (collagen), shrink tissue, or ablate tissue.

Coatings can be applied to the moving components in the catheter to reduce friction. In one embodiment, the sheaths and the torque shaft are coated with a hydrophilic coating (polyvinyl alchohol) to reduce friction between the moving components in the catheter. The coatings can also be hydrophobic (e.g. parylene, PTFE). The coatings can be impregnated with heparin to reduce blood clotting on surface during use.

FIGS. 7A through 7E illustrate additional variations of sweep frames for use with the cutting assemblies and catheters described herein. For purposes of showing the sweep frame, the torque shaft is omitted from the drawings. However, as noted above in FIG. 1B, a torque shaft will extend through the sweep frame where the torque shaft and sweep frame can rotate independently from one another.

Figure 7A:
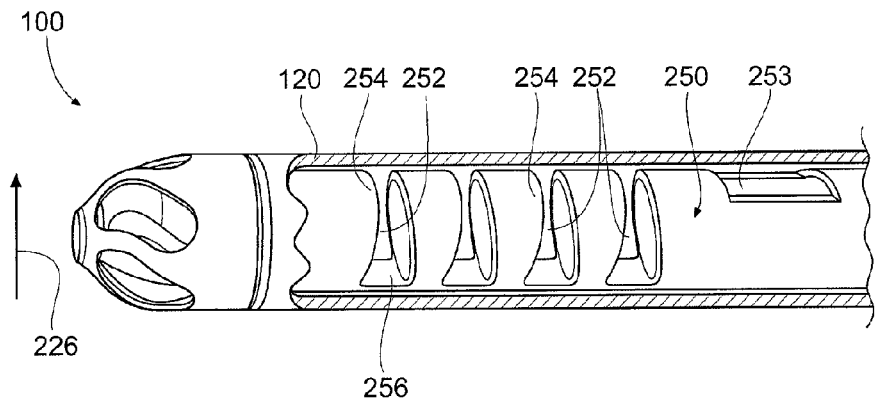
FIG. 7A shows a tissue debulking device having a sweep frame in an unflexed position.

FIG. 7A shows a distal view of a debulking catheter 100 where the catheter body 120 is partially removed to show a variation of a sweep frame 250. In this variation, the sweep frame 250 is constructed from a laser cut tube or sweep tube having serrations, openings, or slots 252. The openings 252 create a weakened section along a first radial side 254 of the sweep tube 250. The side opposite 256 to the first radial side 254 comprises an area of increased column strength. Accordingly, as a physician applies an axial force at the proximal end of the catheter 100, typically via a sweep member as discussed below, the force causes the sweep tube 250 to compress against a fixed area within the catheter 100. As the force compresses the sweep frame 250, the sweep frame 250 is forced to compress at the weakened section along the first radial side 254 causing bending at the continuous area or spine 256 of the sweep frame 250 in the direction indicated by the arrow 262. The fixation area (the area against which the sweep frame encounters resistance) can be the cutter assembly or a distal area on the catheter body 120. However, any area will suffice so long as the sweep frame 250 is able to bend upon the application of force.

The spacing and size of the openings 252 can be selected to allow a pre-determined bend upon deformation of the sweep frame 250. For example, the openings can be selected to limit deflection of the distal end of the catheter to less than 90 degrees or to any angular bend to provide an added safety measure when the device is used within a vessel. Moreover, the spacing between adjacent openings 252 and/or the size of openings can vary in the sweep frame 250. For example, the spacing and/or size of the openings 252 can increase or decrease along the length of the sweep frame 250. In an additional variation, the spacing and the size of the openings can vary inversely along the length of the sweep frame 250.

In the illustrated variation, the size of the openings in the sweep tube 250 decrease in a direction away from the first radial side 254 of the sweep tube 250. This configuration was found to minimize interference with the torque shaft (not shown.)

In addition, the sweep frames 250 described herein can have any number of features to assist in joining the sweep frame 250 to the catheter 100. For example, in those cases where the sweep frame is constructed from a super-elastic or shape memory alloy, the frame 250 can include one or more openings 253 located in a sidewall to increase the bond between the superelastic/shape memory alloy component and a regular metallic shaft.

Figure 7B:
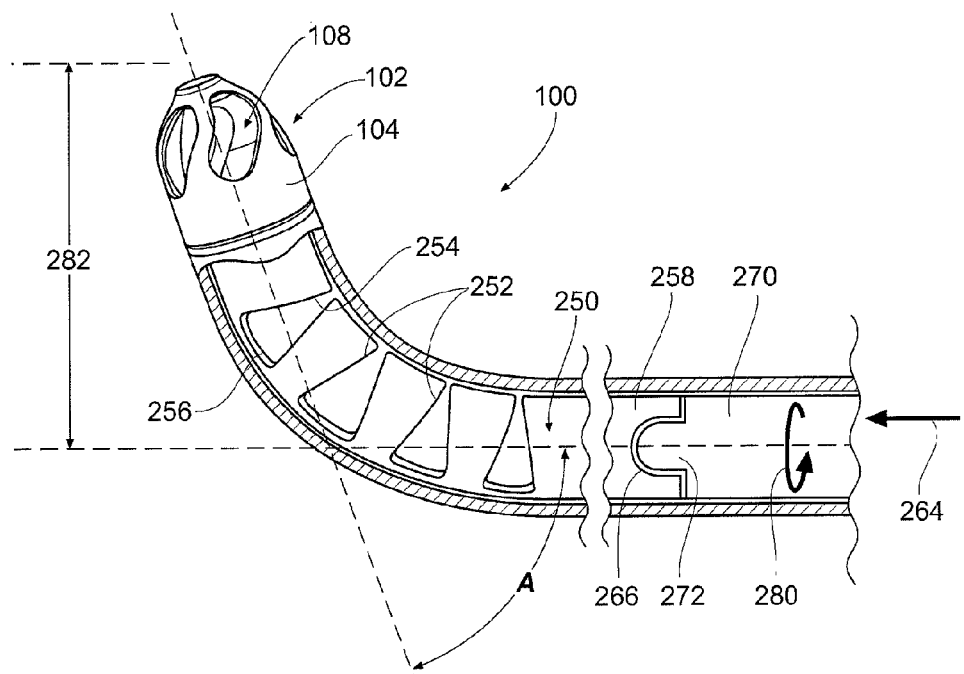
FIG. 7B shows the tissue debulking device of FIG. 7A where the sweep frame is flexed or compressed to articulate the catheter.

FIG. 7B illustrates the tissue debulking catheter 100 upon the application of force indicated in the direction of arrow 264. As noted above, force 264 is applied by the physician at the proximal end or handle of the system 100. In some variations, the force is applied through the use of a sweep member 270 that is axially moveable within the catheter body 120. The sweep member can comprise a tubular structure or a spline or wire that has sufficient column strength to compress as well as rotate the sweep frame 250. Because the distal end of the sweep frame is prevented from moving distally (typically because the cutter assembly is affixed to the catheter body 120), the sweep frame bends at the spine 256 in the direction of the first radial side 254. As shown, the spacing of the openings 252 simply decreases at the first radial side 254. This causes articulation of the cutting assembly 102 so that an axis of the cutting assembly becomes offset from an axis of the proximal end 258 of the sweep frame 250 as denoted by angle A. As noted herein, the angle A is not limited to that shown. Instead, the angle can be predetermined, depending on the construction of a particular sweep frame 250 to provide any angle that is suited for a target vessel or body lumen.

In one variation, the sweep member 270 (also called a sweep shaft) can be fabricated as a hypo-tube structure (constructed from a super-elastic allow or a medical grade stainless steel). The sweep member 270 can have varying degrees of flexibility to allow the catheter 100 to be more flexible at a distal portion and rigid at a proximal portion. This allows for improved navigation through tortuous anatomy as well as improved transmission of torque generated at the proximal end of the device. In additional variations, the sweep-member should not be prone to excessive compression or elongation given that it must transmit the rotational force to the sweep frame.

Upon articulation of the cutting assembly 102, the physician can further rotate the sweep member 270 as shown by arrow 280. Rotation of the sweep member 270 causes rotation of the sweep frame 250 when articulated causing movement of the cutting assembly 102 in an arc-type motion about an axis of the proximal end of the sweep frame 258. This movement causes the cutting assembly to move through an arc having a radius denoted by 282. In some variations of the device, the sweep frame 250 and sweep member 270 can rotate independently of the catheter body 120. However, allowing the catheter body 120 to rotate with the sweep frame 250 and sweep member 270 reduces the resistance on the sweep member 270 as it rotates. In this latter case, the catheter body 120 as well as the cutter housing 104 rotate with the sweep frame 250. However, the rotatable cutter (and the torque shaft—not shown) still rotate independently of the sweep frame 250. Also as noted above, this ability to sweep the cutting assembly 102 in an arc or a circle larger than a diameter of the cutter 102 allows the physician to create a significantly larger opening in the target site than the diameter of the cutting assembly itself. Such a feature eliminates the need to exchange the device for a separate cutting instrument having a larger cutting head. Not only does such a feature save procedure time, but the device is able to create variable sized openings in body lumens.

FIG. 7B also illustrates a variation of the sweep member 270 that can be applied to any variation of the device shown herein. In some cases it may be desirable to disengage the sweep member 270 from the sweep frame 250. In such a case, the sweep member 270 can be axially slidable to disengage the sweep frame 250. However, upon re-engagement with the sweep frame 250, the sweep member 270 must also be able to rotate the sweep frame 250. Accordingly, the sweep frame 250 and sweep member 270 can include one or more keys and key-ways. Although the illustration shows the sweep frame 250 as having a keyway 266 at a proximal end 258 and the sweep member 270 as having a key 272, any type of configuration that allows translation of rotation is within the scope of this disclosure.

Figure 7C:
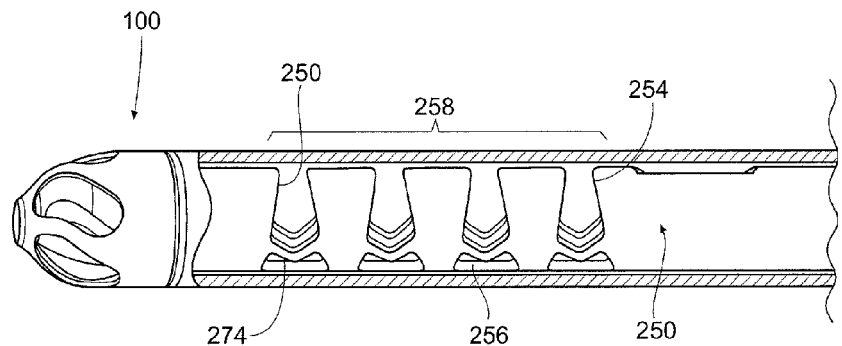
FIGS. 7C-7E show additional variations of sweep members for use with the debulking devices described herein.

FIG. 7C illustrates a variation of a device 100 having sweep frame 250 with a weakened section 268 having a varying column strength. In this variation, the column strength of the sweep frame 250 increases in a circumferential direction away from the first radial side 254. The increase in column strength prevents radial twisting of the sweep frame 250 as it deflects. In the illustrated variation, the sweep frame 250 comprises a plurality of reinforcement arms, ribs, or struts 274 within the openings 250 on the sweep frame 250 where the arms, ribs, or struts 274 are configured to preferentially bend towards the spine 256 as the sweep frame 250 bends. In this variation, the portion containing the arms, ribs, or struts 274 that is adjacent to (but spaced from) the first radial side comprises a second column strength that is greater than the column strength of the radial side but less than a column strength of the remaining spine 256. Again, the varying column strength is intended to prevent twisting of the sweep frame 250 upon deflection.

Figure 7D:
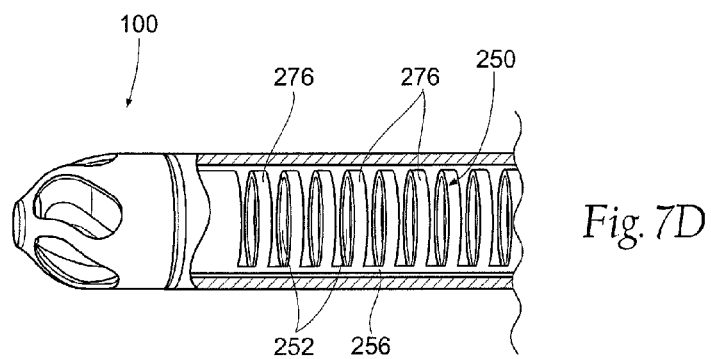

FIG. 7D shows another variation of a sweep frame 250. In this variation, the sweep frame comprises a plurality of rings 276 spaced apart to create the openings 252 within the sweep frame 250. The rings can be joined at the spine area 256 via a separate member, a polymer coating, or a separate frame that is ultimately joined to the rings. As noted above, the rings can be spaced or vary in size to achieve the desired pre-determined curvature upon compression of the sweep frame 250.

Figure 7E:
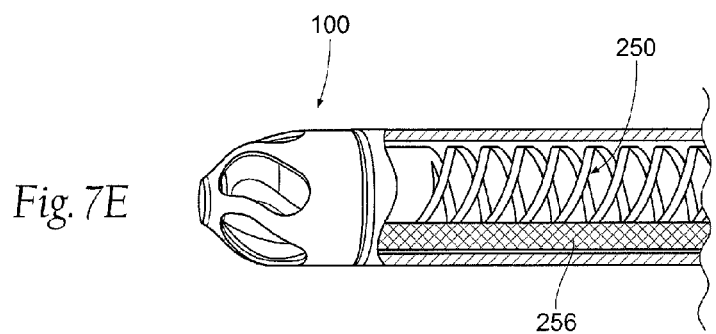

FIG. 7E shows another variation of a sweep frame 250 comprises a woven, coiled, braided or laser cut mesh structure similar to that of a vascular stent. The sweep frame structure can comprise a wire or ribbon material having a reinforced section to function as the spine 256. For example, one side of the stent structure sweep frame 250 can be treated via a coating, fixture or any other means to increase a column strength of the section. Accordingly, this area of the stent structure sweep frame 250 functions as a spine 256 of the sweep frame 250. Although the spine 256 of FIGS. 7D and 7E are shown to be along a bottom portion of the respective sweep frames, the sweep frames can be manufactured to provide varying regions of column strength as described above.

It is understood that the sweep frames can vary from those that are shown to be any structure that allows for preferential bending and rotation when placed within the catheter 100.

The sweep frame can be fabricated from a variety of materials including a shape memory alloy, a super elastic alloy, a medical grade stainless steel, or other polymeric material. The material of the sweep frame 250 can be radiopaque, or can be altered to be radiopaque. In such cases, the physician will be able to observe the degree of articulation of the device by observing the curve of the sweep frame 250 prior to cutting tissue.

In general, for proper debulking of tissue within vessels, a debulking device should have a catheter that is able to support the cutter assembly with sufficient apposition force (bending stiffness). The catheter body must be torqueable enough (i.e., have sufficient torsional stiffness) so that the physician can point the cutter to desired the angular position within the vessel. The debulking device must also be pushable enough (i.e., have sufficient column stiffness) to allow proper cutting as the physician advances the device through tissue. However, these needs must be balanced against making a device that is too stiff to reliably access tortuous or angled anatomy. In order to balance these requirements, a variation of a debulking device can have a more flexible distal tip location (within the last 10 cm) to improve the navigation (trackability over guidewire) in tortuous anatomy. Because the overall stiffness (in compression and torque) depends upon the full length of the catheter, but navigation is influenced mainly by the distal tip region, this method is one way to optimize several variables at the same time.

An additional design for increased torque and push is to construct the catheter body and/or sweep member from a braid over a wound coil, with an optional polymeric jacket covering. This composite construction may be over a polymer liner made of a material such as PTFE. Yet another variation includes a catheter shaft and/or sweep member fabricated from a metal tube having selective cuts along the length of the tube (e.g., stainless steel or nitinol) to create the desired profile of stiffness (bending, torsion, and compression) along the length of the catheter. This slotted metal tube can be lined or jacketed with polymeric material, and further may be treated to produce hydrophilic, hydrophobic, or drug binding (heparin, antimicrobial) properties. The configurations described herein apply to any debulking device described herein.

Figure 7F:
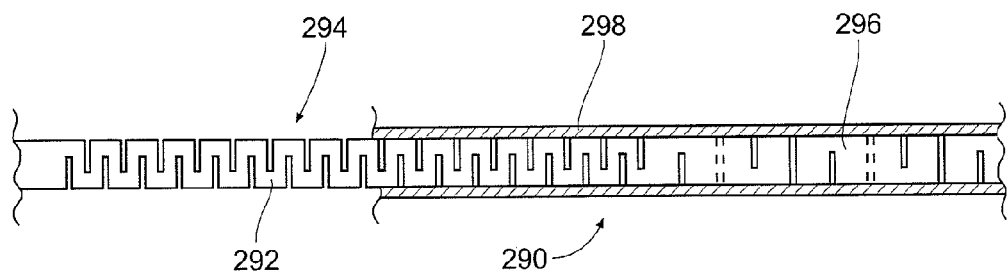
FIGS. 7F-7G show additional possible variations a catheter body or sweep member.
Figure 7G:
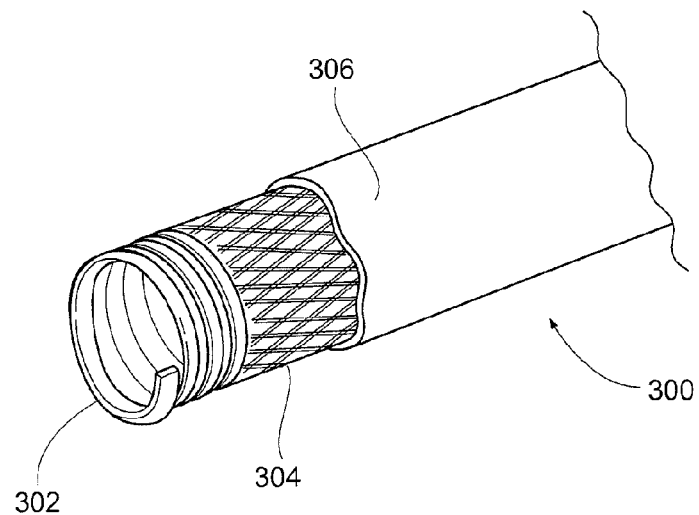

FIGS. 7F and 7G illustrate two possible variations of a composite construction that can be employed in fabricating either a sweep member or a catheter body for use in the debulking devices described herein. FIG. 7F shows a composite construction 290 of a slotted tube 292 (where the tube can be selected from a polymer, a metal—such as stainless steel, or a shape memory alloy—such as a super-elastic Nitinol tube, or a combination therein). The pattern of slots along the tube can be tailored to achieve the desired properties such as graded stiffness along the long axis and/or the short axis of the shaft. The construction 290 can optionally include polymeric coatings, sleeves, or liners 298 in the inner and outer surfaces of the tube. FIG. 7F also shows a tube 292 as having a first region 294 and a second region 296 where the frequency of the slots varies between regions. Any number of slotted tube configurations, such as those found in medical devices designed for navigation to tortuous areas, can be employed in the designs herein. Such designs, when combined in debulking catheters with sweep frames as described herein, provide significant and unexpected improvements in steering and cutting of tissue.

FIG. 7G illustrates yet another variation of a composite construction 300 that can be employed in sweep members and catheter bodies for use with variations of the debulking devices described herein. As illustrated, the construction 300 includes a coil member 302 covered by a braid 304. The coil and braid can each be fabricated from any material commonly known in the field of braided/coiled catheters. For example, the coil 302 can be wound from a super-elastic wire or ribbon. While the braid can comprise a plurality of super elastic or stainless steel filaments braided or woven together. FIG. 7G also shows the braid 304 covered by a polymeric coating, sleeve, or liner 306.

In an additional variation, the sweep frame and/or sweep member can comprise a spiral cut tube covered by a liner or polymeric layer. In such a case, the angle of the spiral as well as the width can be selected to impart desired characteristics on the device. For example, the spiral can be selected to maximize pushability of the device while maintaining a near one-to-one relationship between the cutting assembly and proximal end of the device when rotating or sweeping the cutting assembly.

Figure 7H:
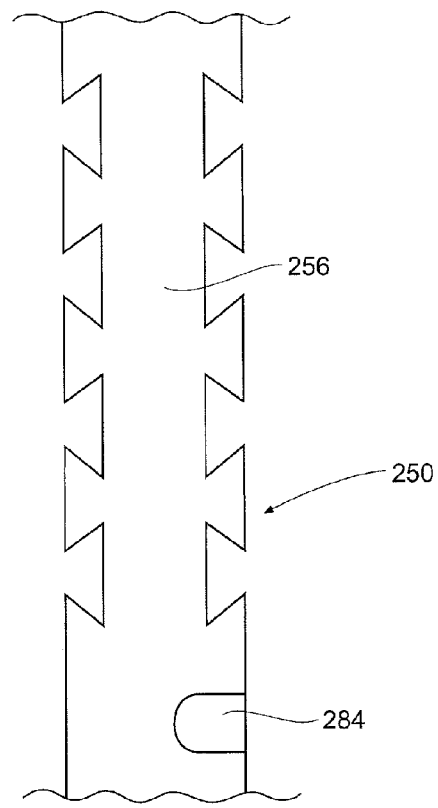
FIGS. 7H-7I show variations of a sweep frame having a visualization feature that permits a physician to determine orientation and direction of articulation of the cutting assembly when the device is viewed under non-invasive imaging.
Figure 7I:
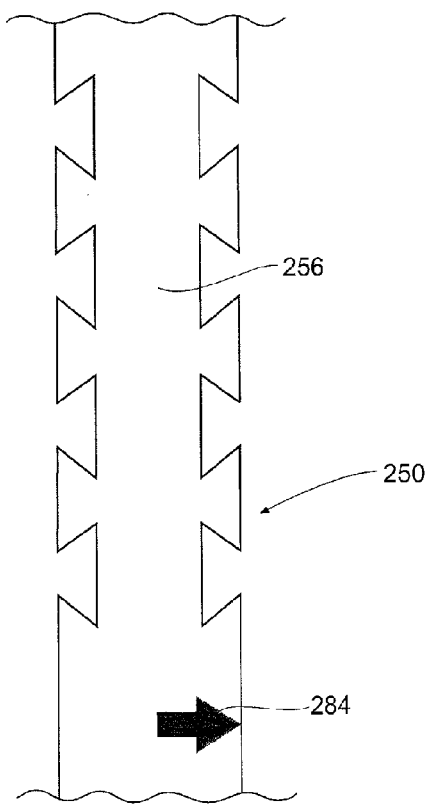

FIGS. 7H-7I show variations of a sweep frame 250 having a visualization feature 284 that permits a physician to determine orientation and direction of articulation of the cutting assembly when the device is viewed under non-invasive imaging. In FIG. 7H shows one variation of the visualization feature 284 as being a notch or opening on a side of the sweep frame 250 that is perpendicular to the direction in which the frame bends. In one example, the visualization mark is placed 90 degrees relative to the spine 256. Although the feature 284 is shown on the right side of the sweep frame 250, any side may be used so long as the location and orientation of the feature 284 conveys to the physician the orientation and direction of bend of the sweep frame 250 via non-invasive imaging. FIG. 7I illustrates another variation of an orientation feature 284 comprising a marking substance (either a radiopaque additive or a highly radiopaque metal deposited on the sweep frame 250). In any case, the visualization feature must provide sufficient contrast against the frame 250 when viewed in a non-invasive imaging modality. The feature can also comprise a structure selected from the group consisting of a notch, opening, tab, protrusion, or deposition.

As shown, both visualization features 284 are on the right-hand side of the sweep frame 250 when the spine 256 of the frame 250 is directly adjacent to the physician. In this position, articulation of the sweep frame (that occurs in a direction away from the spine), causes the sweep frame 250 to deflect away from the physician. Accordingly, when the physician observes the visualization marks 284 to the right of the device, the physician will know that flexure of the sweep frame 250 will occur directly away from the physician. Clearly, the present invention includes any number of visualization features or placement of such features on any portion of the sweep frame so long as the physician will be able to determine the orientation and direction of bend of the sweep frame from viewing the visualization mark(s) 284.

Figure 8A:
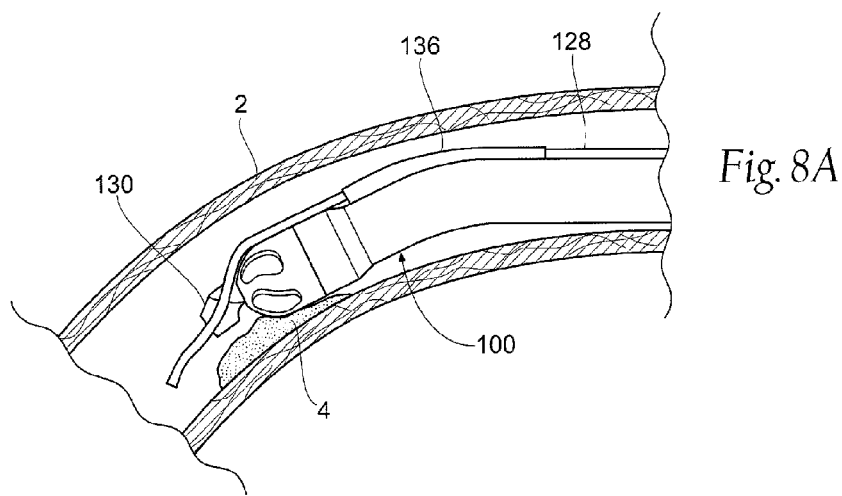
FIG. 8A shows a variation of a device configured for rapid exchange.

FIG. 8A illustrates a variation of a device 100 configured for rapid exchange. As shown, the device 100 includes a short passage, lumen, or other track 136 for the purpose of advancing the device 100 over a guidewire 128. However, the track 136 does not extend along the entire length of the device 100. Moreover, an additional portion of the track 136 may be located at a distal end of the catheter to center a guidewire 128.

This feature permits rapid decoupling of the device 100 and guidewire 128 by merely holding the guidewire still and pulling or pushing the catheter 100 over the guidewire. One benefit of such a feature is that the guidewire 128 may remain close to the site while being decoupled from the device 100. Accordingly, the surgeon can advance additional devices over the guidewire and to the site in a rapid fashion. This configuration allows for quick separation of the catheter from the wire and introduction of another catheter over the wire since most of the wire is outside of the catheter.

Figure 8B:
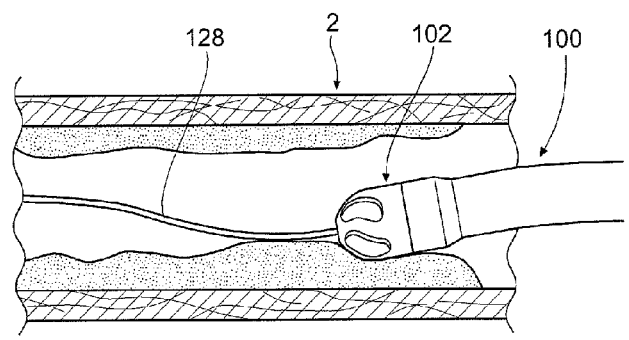
FIG. 8B illustrates an example of centering a tip of a cutting assembly over a guide wire.

As shown in FIG. 8B, centering the tip of the cutting assembly 102 over a guide wire 128 improves the control, access and positioning of the cutting assembly 102 relative to a body lumen or vessel 2. To accomplish this, the cutting assembly 102 can have a central lumen to accommodate a guide wire 128. Variations of the device 100 include a central guide wire lumen that runs the length of the catheter through all central components including the torque shaft and the cutter. As noted above, a guidewire 128 can be affixed to the housing 104 or other non-rotational component of the cutting assembly 102. In such a case, the guidewire 128 may preferably be a short segment that assists with navigation of the device through an occluded portion of a body lumen. However, the devices 100 can also operate without a guidewire since the head is steerable like a guidewire.

Figure 9A:
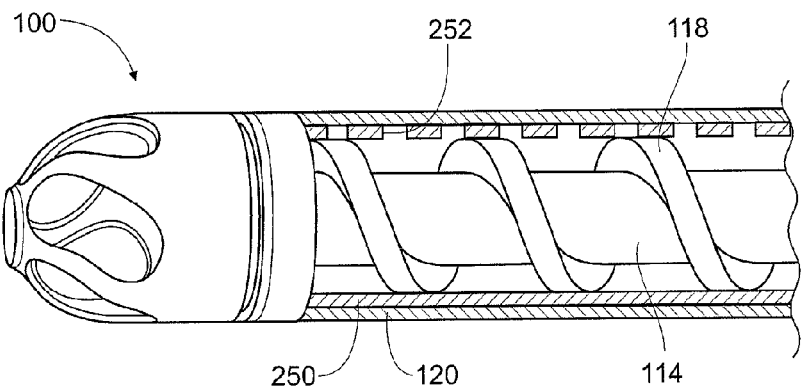
FIG. 9A shows a conveyor within the catheter body and sweep frame.

FIG. 9A illustrates a partial cross-sectional view of a variation of a device 100 showing the placement of a torque shaft 114 within the catheter body 120 and sweep frame 250. As shown, this variation of the device 100 includes a conveyor member 118 located within the device 100 and on an exterior surface of the torque shaft 114. The conveyor member 118 may be an auger type system or an Archimedes-type screw that conveys the debris and material generated during the procedure away from the operative site. In any case, the conveying member 118 will have a raised surface or blade that drives materials in a proximal direction away from the operative site. Such materials may be conveyed to a receptacle outside of the body or such materials may be stored within the device 100. In one variation, the torque shaft 114 and conveying member 118 extend along the length of the catheter. As shown, the torque shaft 114 and conveyor 118 fit within the sweep frame 250. In some variations of the device, a cover or film can be placed between the sweep frame 250 and torque shaft 114 to prevent debris from becoming trapped within the serrations, slots or openings 252 of the sweep frame 250. The cover or film also acts as a smooth, low friction surface.

Figure 9B:
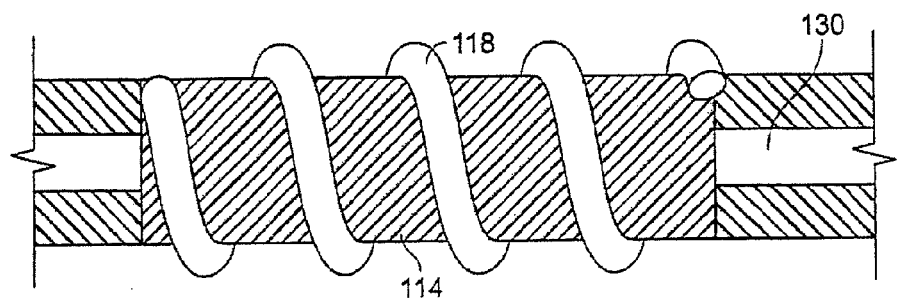
FIG. 9B shows a partial cross sectional view of a variation of a torque shaft having counter wound coils.

FIG. 9B shows a partial sectional view of an example of a torque shaft 114 for coupling to a cutter assembly. To aid in removal of materials, the torque shaft can be a set of counter-wound coils, with the outer coil wound at the proper (greater) pitch to form the conveying member 118. Winding the coils counter to each other automatically reinforces the torque shaft 114 during rotation. Alternatively, the torque shaft 114 may be made out of a rigid plastic, rendered flexible by incorporation of a spiral relief or groove which acts as a conveying member 118. Although the shaft may be fabricated from any standard material, variations of the shaft include a metal braid embedded in polymer (PEBAX, polyurethane, polyethylene, fluoropolymers, parylene, polyimide, PEEK, PET) or one or more metal coils embedded in a polymer such as PEBAX, polyurethane, polyethylene, fluoropolymers, parylene, polyimide, PEEK, PET. These constructions maximize torsional strength and stiffness, as well as column strength for "pushability", and minimize bending stiffness for flexibility. Such features are important for navigation of the catheter through tortuous vessels but allow for smooth transmission of torque over the long length of the catheter. In the multi-coil construction, the inner coil should be wound in the same sense as that of the rotation so that it would tend to open up under torque resistance. This ensures that the guidewire lumen remain patent during rotation. The next coil should be wound opposite the inner to counter the expansion to keep the inner coil from binding up against the outer catheter tube.

FIG. 9B also shows a torque shaft 114 having a central lumen 130. Typically the lumen will be used to deliver a guidewire. In such cases, the central lumen may be coated with a lubricious material (such as a hydrophilic coating or Parylene) or made of a lubricious material such as PTFE to avoid binding with the guidewire. However, in some variations a guidewire section is affixed to a distal end of the housing. Moreover, the central lumen of the torque shaft 114 may also be used to deliver fluids to the operative site simultaneously with the guidewire or in place of the guidewire.

Figure 9C:
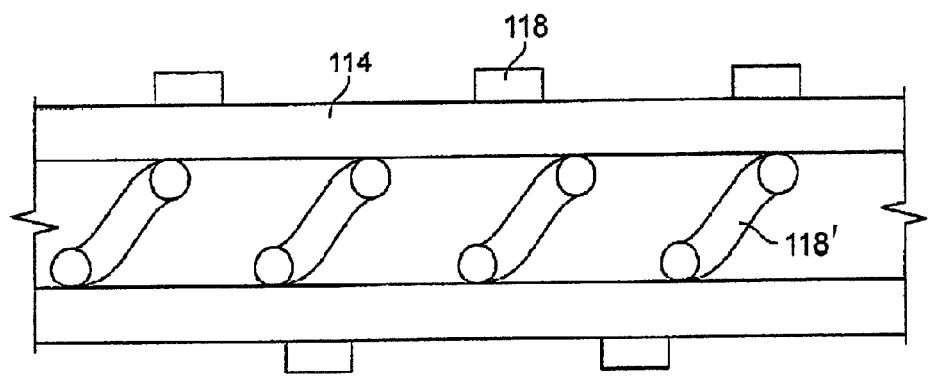
FIG. 9C shows a second conveyor within a torque shaft.

In some variations, the conveying member 118 may be integral to the shaft 114 (such as by cutting the conveying member 118 into the torque shaft 114 or by extruding the torque shaft 114 directly with a helical groove or protrusion. In an additional variation as shown in FIG. 9C, an additional conveying member 118 may be incorporated on an inside of the torque shaft, where the internal conveying member is wound opposite to that of the external conveying member 118. Such a configuration allows for aspiration and debris (via the external conveying member 118) and infusion (via the internal conveying member 118). Such a dual action can enhance the ability to excise and aspirate plaque by: (1) thinning the blood, whether by viscosity alone or with the addition of anti-coagulants such as heparin or warfarin (cumadin), and/or anti-platetlet drugs such as Clopidogrel, (2) improving the pumpability (aspirability) of the excised plaque by converting it into a solid-liquid slurry that exhibits greater pumping efficiency, and (3) establishing a flow-controlled secondary method of trapping emboli that are not sheared directly into the housing, by establishing a local recirculation zone.

As noted above, the conveying member 118 can be wound in the same directional sense as the cutter 108 and in the same direction of rotation to effect aspiration of tissue debris. The impeller action of the cutter 108 moves the tissue debris from inside the housing 104 openings 106 into the torque shaft. The pitch of the cutting edges 112 may be matched in to that of the conveying member 118 to further optimize aspiration. Alternatively, the pitch of the conveying member 118 may be changed to increase the speed at which material moves once it enters the conveying member 118. As discussed herein, debris can be evacuated outside the body by the conveying member 118 action along the length of the catheter and with or without supplement of the vacuum 152 pump connected to the catheter handle. Alternatively, the debris may be accumulated in a reservoir within the device.

Figure 10A:
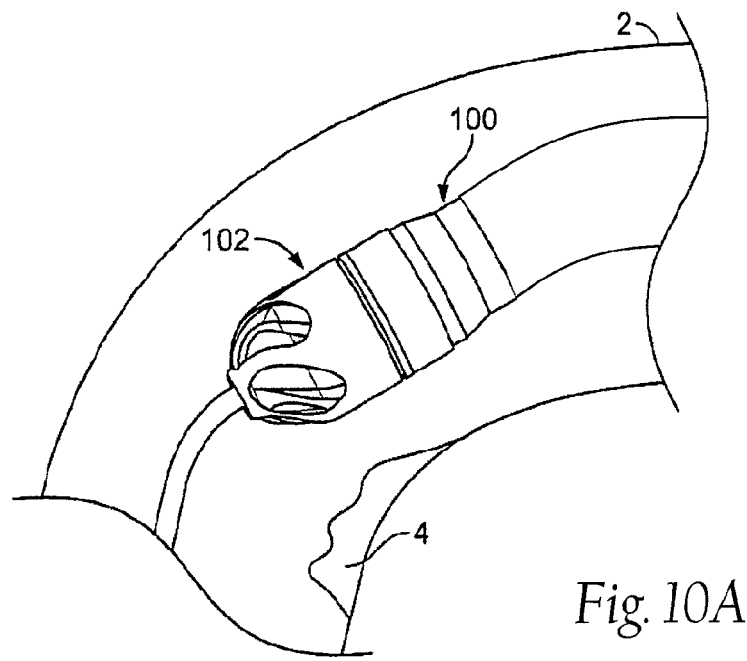
FIG. 10A illustrates articulation of a tip of the device.

FIG. 10A illustrates an example of a variation of a device 100 being steered when using the sweep frame and sweep member described above. The ability to steer the tip of the device 100 is useful under a number of conditions. For example, when debulking an eccentric lesion as shown, the cutting assembly 102 should be pointed towards the side of the vessel 2 having the greater amount of stenotic material 4. Naturally, this orientation helps prevent cutting into the bare wall/vessel 2 and focuses the cutting on stenotic tissue 4. When in a curved section of the vessel 2, without the ability to steer, the cutting assembly 102 would tend to bias towards the outside of the curve. As shown in FIG. 10A, steering allows the cutting assembly 102 to point inward to avoid accidental cutting of vessel wall 2.

Figure 10B:
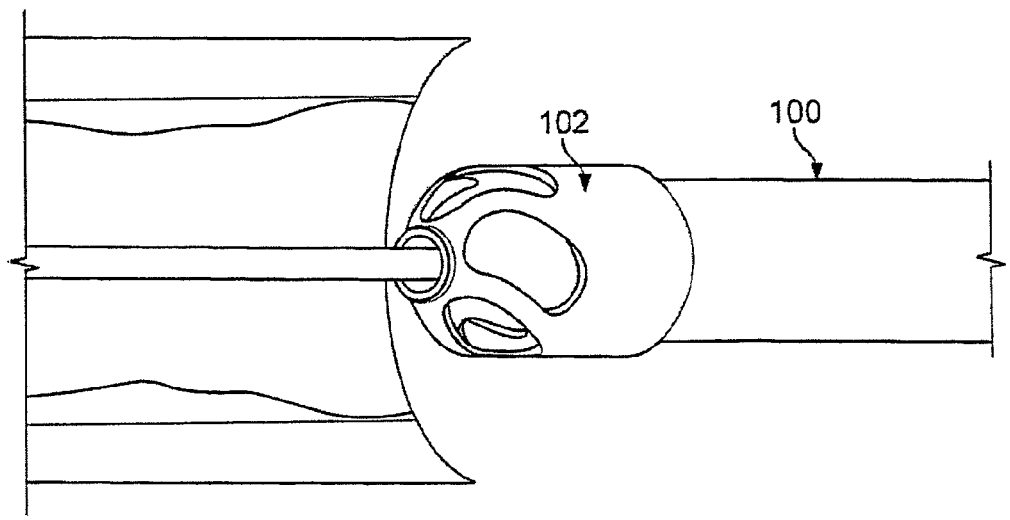
FIG. 10B-10D shows sweeping of the cutting assembly.
Figure 10C:
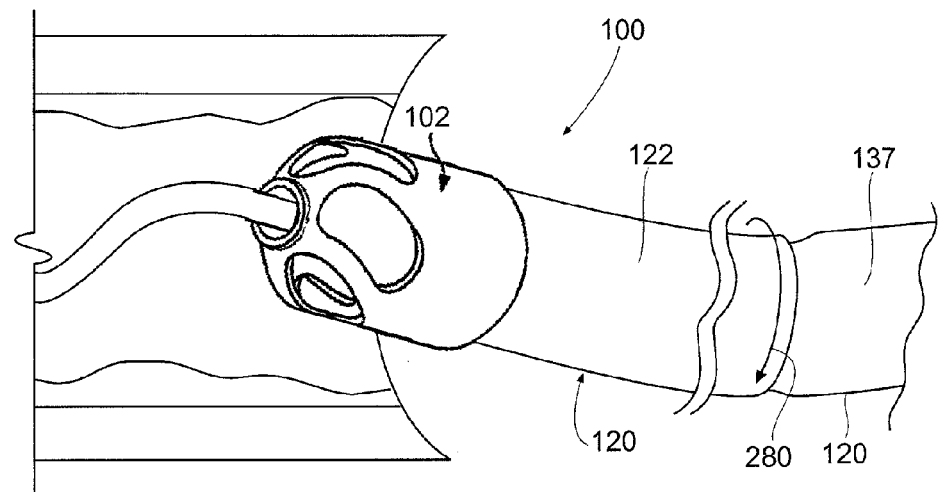
Figure 10D:
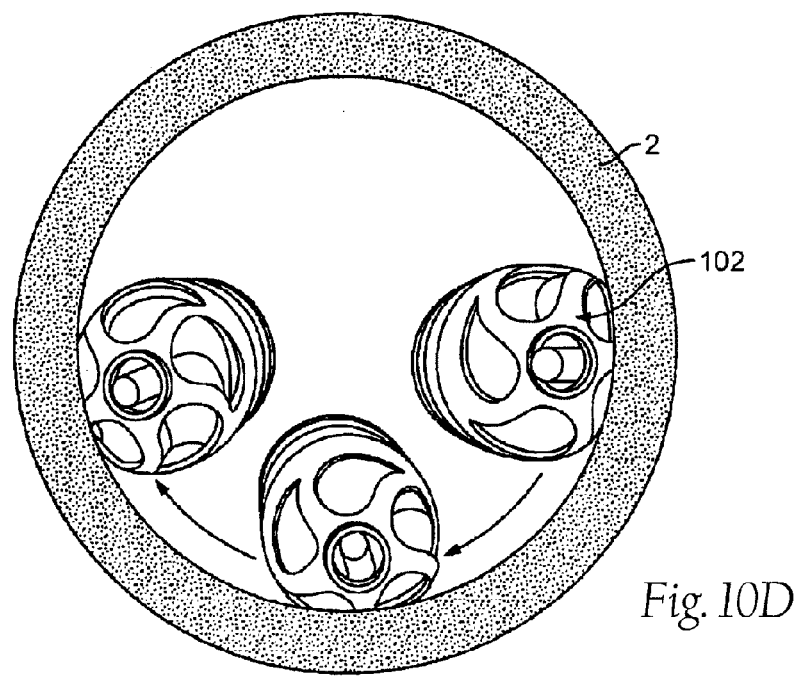

The ability to steer the device 100 also allows for a sweeping motion when cutting occlusive material. FIG. 10B shows the rotation of the cutting assembly 102. As shown in FIG. 10C, when the cutting assembly 102 deflects relative to the axis of the catheter, rotation of the deflected portion 102 creates a sweeping motion. It is noted that rotation or articulation of the cutting assembly also includes rotation or articulation of the catheter to allow the cutting assembly to deflect relative to an axis of the catheter. FIG. 10D shows a front view taken along an axis of the vessel to illustrate the sweeping motion causing the cutting assembly 102 to "sweep" over a larger region than the diameter of the cutting assembly. In most cases, when articulated, the device will be rotated to sweep over an arc or even a full circle. The rotation of the cutter may or may not be independent of the rotation of the device. A user of the device may couple the sweeping motion of the cutting assembly with axial translation of the catheter for efficient creation of a larger diameter opening over a length of the occluded vessel. The combination of movement can be performed when the device is placed over a guidewire, for example by the use of a lead screw in the proximal handle assembly of the device. In another aspect of the devices described herein, the angle of articulation may be fixed so that the device sweeps in a uniform manner when rotated.

FIG. 10C also shows a variation of a debulking device having a catheter body 120 where a first or distal portion 122 of the catheter body rotates 280 as the cutting assembly sweeps in an arc. The second portion 137 of the catheter remains stationary. Accordingly, the two part catheter may be joined to permit the relative movement between sections. The second portion 137 may incorporate a sweep frame and sweep shaft.

Figure 11A:
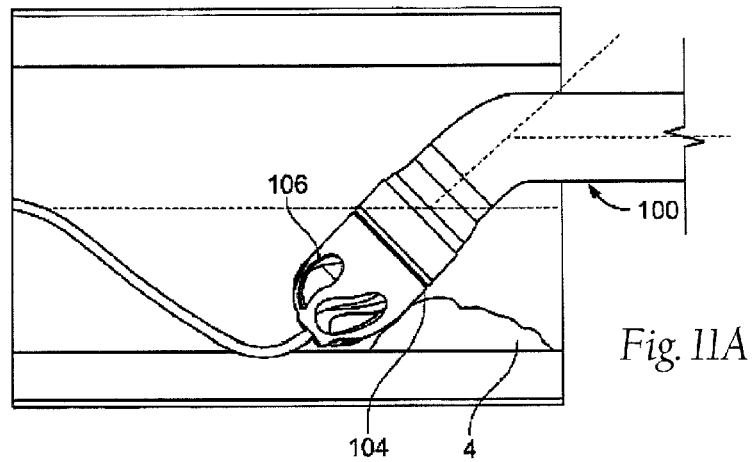
FIG. 11A shows placement of housing windows to prevent damage to the vessel walls.

In addition, the shape of the housing 104 as well as the location of the windows 106 can be chosen so that when the device 100 is substantially aligned with the lesion, or engages it at less than some critical attack angle, it will cut effectively. However, when pivoted at an angle greater than the critical angle, the cutting edges or grinding element will not engage the lesion as shown in FIG. 11A. This means that at large deflections, as the catheter tip approaches the vessel wall, it automatically reduces its depth of cut and ultimately will not cut when the critical angle is exceeded. For example, the cutter distal tip is blunt and does not cut. As the catheter tip is deflected outward, the blunt tip contacts the vessel and keeps the cutting edges proximal to the tip from contacting the vessel wall. Also the wire in combination with the device can also act as a buffer to prevent the cutting edges from reaching the vessel. As shown, the portion of the guidewire that extends from the housing 104 will bend at a minimum bend radius. This permits a portion of the wire closest to the housing to act as a bumper and prevents the cutter and windows from engaging the walls of the vessel. In certain variations, wires with varying bend radii can be selected to offer varying degrees of protection by spacing the cutting head away from the tissue wall.

Figure 11B:
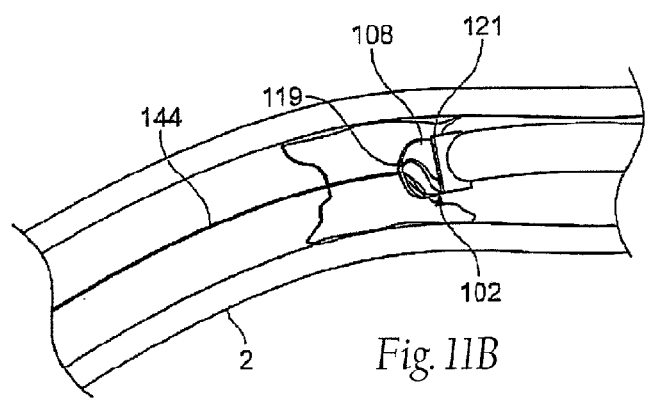
FIGS. 11B-11C shows placement of features of the cutter assembly that prevent damage to the vessel walls.
Figure 11C:
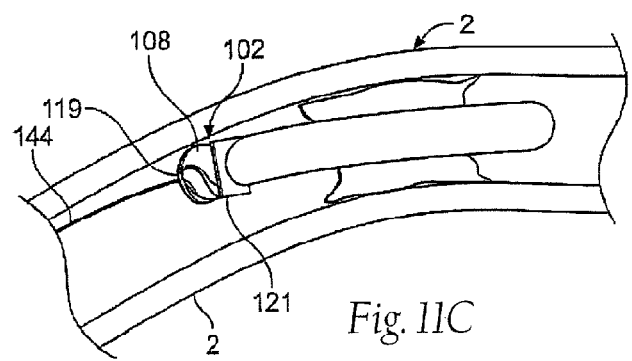

FIGS. 11B and 11C show a cutter assembly design that is specialized for forward cutting. This particular variation includes an open ended housing where the cutter extends from the housing (as shown above). However, a blunt bumper 119 at the tip of the cutter 108 acts as a buffer to prevent accidental cutting into the guidewire 144 or excessively into the lumen wall 2. In addition, this design can optionally incorporate a static housing portion 121 on a back end of the cutter assembly 102 that partially shields the cutter from deep side cuts into the lumen wall 2.

As shown above, the catheter body 120 can remains stationary while the inner sweep frame 250 and sweep member 270 rotate to move the cutting assembly 102 in an arc or orbit within the lumen. Alternatively, the sweep frame 250 and sweep member 270 can rotate with the catheter body 120 but independently of the cutting assembly and torque shaft. The outer sheath is preferably composed of a metal braid sandwiched in a polymeric matrix of such materials as high density polyethylene (HDPE), polyethylene (PE), fluoro-polymer (PTFE), nylon, polyether-block amide (PEBAX), polyurethane, and/or silicone. The sheath is stiffer proximally than distally. This can be achieved by using softer grades of polymers distally and/or having no metal braid distally.

FIGS. 12A and 12B illustrate one variation of a control system or fixture. As shown, the control system 200 includes a sweep control knob 202 coupled to the sweep member as discussed above. The sweep control knob 202 can axially advance the sweep member to cause deflection of the sweep frame. In addition, the sweep control knob 202 can rotate independently relative torque shaft and rotatable cutter in the cutting assembly 102. Again, the sweep sheath can be composed of a super-elastic alloy, a medical grade stainless steel, a metal braid sandwiched in a polymeric matrix of such materials as polyethylene (PE), fluoro-polymer (PTFE), nylon, and/or polyether-block amide (PEBAX), polyurethane, and/or silicone. The sweep sheath can also be made of counter wound metal coils. Its distal end is curved and is preferably made of a material that can withstand high degree of flex and retain its curved shape. Such material may include polymers such as PE, nylon, Polyetheretherketone (PEEK), Nickel Titanium (Nitinol), or spring steel.

As shown in FIG. 12G, to allow the cutter assembly 102 to be straight and undeflected, the sweep sheath is withdrawn proximally by the sweep control knob 202. This causes removal of the axial force from the sweep frame (in some variations, the sweep frame can be set in a straight configuration). As shown in FIG. 12A, distal movement of the sweep control knob 202 advances the sweep sheath to deflect the catheter tip. The degree of the deflection is controlled by the amount the sweep sheath is advanced. The axial advancement of the sweep sheath is limited by the maximum deflection of the sweep frame.

As shown in FIG. 12B, the sweep control knob 202 can be rotated to sweep the cutting assembly 102 in an arc manner. Although sweeping of the cutting assembly 102 can occur via manual operation. Variations of the device include sweep members that can be selectively coupled to a motor to activate an automated rotation. This allows the physician to have a smooth, continuous, automated means to sweep the cutter without any manual effort.

FIGS. 12A and 12 B also show the catheter 120 as having a flush port 129. The flush port 129 provides a means for injecting a fluid such as heparinized saline or any other medicine into the catheter body 120 to keep blood and tissue debris from clogging the space between components in the device. The flush port 129 can also help lubricate moving components within the device. One desirable fluid path is along the length of the catheter in the space between the catheter body 120 and sweep member 270. Drugs or fluids can be introduced via the flush port 129 for flow out of one or more openings 131 near the catheter tip or cutting assembly 102. Drugs flushing out near the cutting assembly can then infuse into the vessel wall. Using a stenosis-inhibiting drug like paclitaxel or rapamycin could help prevent restenosis after the atherectomy procedure.

Figure 12C:
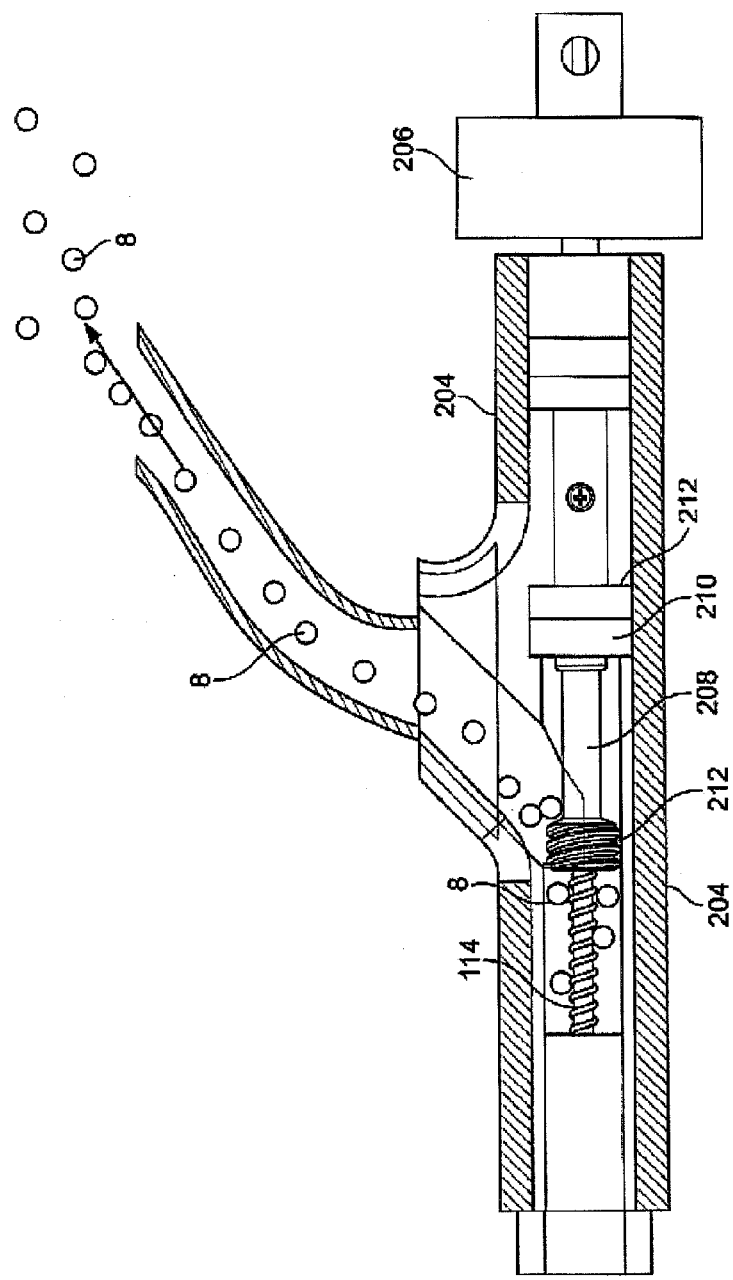
FIG. 12C shows a cross sectional view of a portion of the catheter hub mechanism that removes debris from the device.

Turning now to a variation of the catheter 100 and control system 200, the entire system is arranged from distal to proximal with a cutter assembly 102, a catheter body 120, a flush port 129, a control system 200 for tip deflection and sweep control, a hub 204 or other connection for providing aspiration of the cut materials as well as a drive gear 206 to turn the torque shaft and cutter. The gear 206 is connected to a rigid drive shaft 208 encased within the hub 204 as shown in FIG. 12C. The drive shaft 208 can take a form of a hollow tube with a central lumen for passage of the guidewire and is centered within a lumen in the hub 204 and fixed axially by a pair of bearings 210. A seal 211 adjacent to the bearing 210 prevents aspirated tissue debris from leaking proximally through the bearing 210. A transfer propeller 212 is rigidly attached to the distal portion of the drive shaft 208 to pump aspirated tissue debris 8 from the catheter out into an attached aspiration reservoir. The drive shaft 208 is connected to flexible torque shaft 114 that extends the length of the catheter body for the purpose of transfer torque from the drive shaft to the cutter. As noted above, the torque shaft 114 has helical grooves on its outer diameter and central guidewire lumen. During a procedure run, a motor drives the gear 206 to rotate. This causes rotation of the drive shaft 208, the transfer propeller 212, the torque shaft 114, and the cutter (not shown) all in the same rotational sense. Thus the cutter assembly effectively cuts plaque and drives the debris back into the helical groove on the torque shaft 114. The rotating helical grooves winds the debris back into the hub 204, which is then transferred to the aspiration reservoir by the transfer propeller 212. The propeller 212 can take the form of a screw or a series of circumferentially arranged angled fan blades. The cutter is preferably rotated at a speed of 10,000-25,000 rpm. An alternative design would have the aspiration reservoir built into the hub of the catheter.

As noted above, selecting a desired profile for bending, torsion and axial strength characteristics when designing the catheter body and/or sweep member improves the overall function of the debulking catheter. Aside from the improved ability to advance the cutting assembly and sweep the cutting assembly in an arc-type motion, the proper characteristics improve the ability of the physician to steer the device. For example, selection of the proper characteristics reduces the chance that the distal portion of the device rotates more or less than the proximal end or control knob.

It was found that the devices of the present invention allow a physician to accurately determine the rotation of the cutting assembly since the rotation of the cutting assembly closely corresponds to the rotation of the proximal end or control knob. Such close correspondence is not available unless the catheter body and/or sweep member has sufficient bending, torsion and axial strength characteristics. Accordingly, a further aspect of the debulking devices occurs when these catheter bodies/sweep members are coupled to a system having a sweep control knob 202 that enables indexing and monitoring of the orientation of the cutter assembly. Clearly, this one-to-one relationship can be lost when the distal end or cutting assembly encounters sufficient resistance against or within a lesion, occlusion, or diseased tissue. However, in such cases, the device is still able to debulk tissue and perform its function even though the response may not be one-to-one. In any case, the ability to maintain a near one-to-one relationship and minimize rotational misalignment between the ends of the device allows for steering of the debulking device towards the treatment site.

Figure 12D:
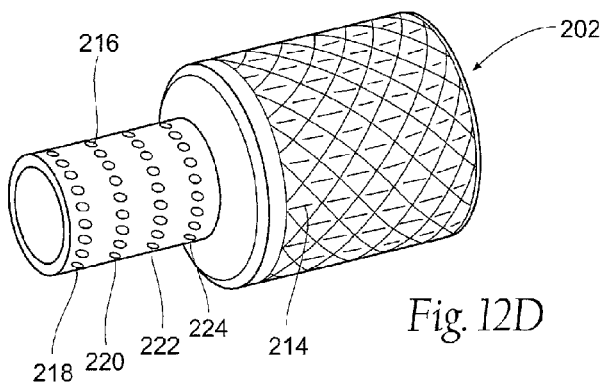
FIGS. 12D-12F shows a variation of a control knob having indexing features.

FIG. 12D shows a conceptual illustration a control knob 202 allowing for indexing of the cutting assembly. As shown, the control knob 200 includes an orientation marker 214 that shall correspond to the weakened section of the sweep frame (not shown). As discussed above, the orientation marker 214 shall also correspond to a side of the sweep frame that is opposite to a spine of the sweep frame. Because the orientation marker 214 is aligned with the sweep frame in such a manner, the physician knows that the device shall bend in a direction corresponding to the orientation marker 214. This allows the physician to identify the orientation of the cutting assembly as it sweeps within the body by observing the orientation of the orientation marker as the physician rotates the sweep control knob 202. Even when the one-to-one relationship is lost (as noted above), the indexing knob adds a fine control to direct the distal end in defined steps or increments. This control can be useful because the physician can direct the cutter within the immediate vicinity to work on areas that need to be resected, versus losing position due to excessive movement. An atherectomy or tissue debulking device having features that allow pushability as well as torsional strength allow the physician greater feedback and control when trying to steer the cutting assembly towards a desired path within the body.

The sweep control knob 202 can also include a plurality of indexing stops or divots 216. Although this variation of the device contains divots, These indexing stops 216 can have a twofold benefit. First, they allow incremental rotational indexing as the physician rotates the knob 202. This incremental indexing is permitted due to the bending, torsion and axial strength characteristics of the device permitting little or no misalignment between the ends of the device. A secondary advantage of the indexing stops 216 is that they allow incremental axial indexing as the physician advances the knob 202 in an axial direction to bend or steer the distal end of the debulking catheter by moving the sweep member 270 in an axially distal direction.

Figure 12E:
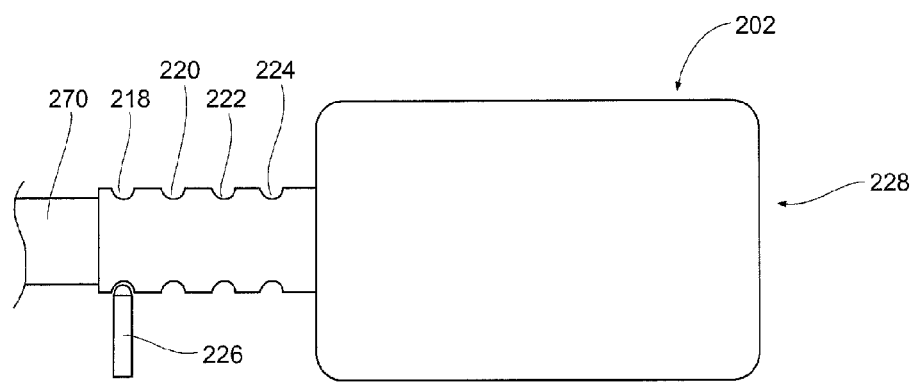
Figure 12F:
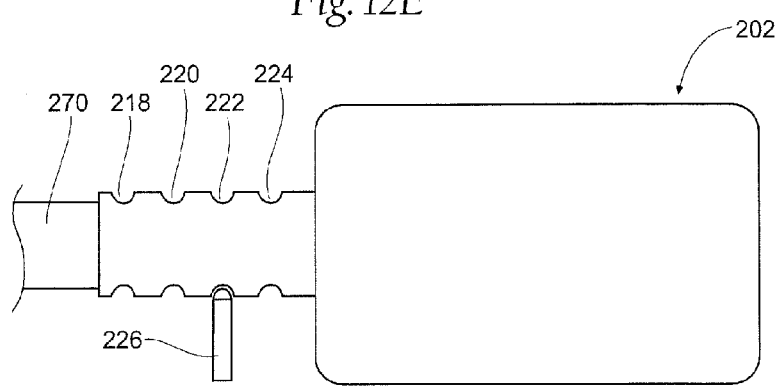

As shown, any number of positions 218, 220, 222, 224 can be created on the knob 202. As shown in FIG. 12E, a spring pin 226 can provide tactile feedback to the physician as the knob 202 rotates. Once the physician desires to bend or steer the debulking device by moving the knob 202 in an axial direction 228, the physician shall feel movement of the knob into the second 220 and third 222 stop positions as shown in FIG. 12F.

Additional components may be incorporated into the devices described herein. For example, it can be desirable to incorporate transducers into the distal region of the catheter to characterize the plaque or to assess plaque and wall thickness and vessel diameter for treatment planning; also transducers may be desired to indicate the progression of debulking or proximity of cutter to vessel wall. For example, pressure sensors mounted on the catheter housing can sense the increase in contact force encountered in the event that the housing is pressed against the vessel wall. Temperature sensors can be used to detect vulnerable plaque. Ultrasound transducers can be used to image luminal area, plaque thickness or volume, and wall thickness. Optical coherence tomography can be used to make plaque and wall thickness measurements. Electrodes can be used for sensing the impedance of contacted tissue, which allows discrimination between types of plaque and also vessel wall. Electrodes can also be used to deliver impulses of energy, for example to assess innervation, to either stimulate or inactivate smooth muscle, or to characterize the plaque (composition, thickness, etc.). For example, transient spasm may be introduced to bring the vessel to a smaller diameter easier to debulk, then reversed either electrically or pharmaceutically. Electrical energy may also be delivered to improve the delivery of drugs or biologic agents, by causing the cell membrane to open in response to the electric stimulation (electroporation). One method of characterization by electrical measurement is electrical impedance tomography.

As shown in FIG. 13, a cutter assembly 102 can also have a burr protruding out its nose. Although the burr 180 may have any type of abrasive surface, in one variation, this burr is blunt and has fine grit (such as diamond grit) to allow for grinding of heavily calcified tissue without injuring adjacent soft tissue. This combination of a burr and cutter allow the distal assembly to remove hard stenotic tissue (calcified plaque) using the burr while the sharp-edged shaving cutter removes softer tissue such as fibrous, fatty tissue, smooth muscle proliferation, or thrombus. In variations, the burr can also have helical flutes to help with aspiration, or the burr can be incorporated to a portion of the cutting edge (for example, the most distal aspect of the cutter).

Infusing solutions (flush) into the target treatment site may be desirable. Infused cool saline can prevent heating of blood and other tissue, which reduces the possibility of thrombus or other tissue damage. Heparinized saline can also prevent thrombus and thin out the blood to help maximize effectiveness of aspiration. The flush can also include drugs such as Clopidogrel, Rapamycin, Paclitaxel or other restenosis-inhibitors. This may help to prevent restenosis and may result in better long term patency. The flush may include paralytics or long-acting smooth muscle relaxants to prevent acute recoil of the vessel. FIGS. 14A-14C illustrate variations of flushing out the device 100. The flush can be infused through the guide wire lumen (FIG. 14A), a side lumen in the catheter shaft (FIG. 14B) or tube, the space between the flexing sheath and the catheter and/or the sideports in the guidewire (FIG. 14C). Flush can come out of a port at the distal end of the cutter pointing the flush proximally to facility aspiration. Alternatively, by instilling the flush out the distal end of the cutter housing over the rounded surface, the flow may be directed rearward by the Coanda effect. The restenosis-inhibitors can be carried by microcapsules with tissue adhesives or velcro-like features on the surface to stick to inner vessel surface so that the drug adheres to the treatment site, and to provide a time-release controlled by the resorption or dissolving of the coating to further improve efficacy. Such velcro-like features may be constructed with nanoscale structures made of organic or inorganic materials. Reducing the volume of foreign matter and exposing remaining tissue and extracellular matrix to drugs, stimulation, or sensors can make any of these techniques more effective.

Another way to infuse fluid is to supply pressurized fluid at the proximal portion of the guidewire lumen (gravity or pressure feed) intravenous bag, for example. A hemostatic seal with a side branch is useful for this purpose; tuohy-borst adapters are one example of a means to implement this.

Balancing the relative amount of infusion versus fluid volume aspirated allows control over the vessel diameter; aspirating more fluid than is instilled will evacuate the vessel, shrinking its diameter, and allow cutting of lesion at a greater diameter than the atherectomy catheter. This has been a problem for certain open cutter designs that use aspiration, because the aggressive aspiration required to trap the embolic particles evacuates and collapses the artery around the cutter blades; this is both a performance issue because the cutter can bog down from too high torque load, and the cutter can easily perforate the vessel. The shielded design described here obviates both problems, and further requires less aggressive aspiration to be effective, giving a wider range of control to the user.

The devices of the present invention may also be used in conjunction with other structures placed in the body lumens. For example, as shown in FIG. 15, one way to protect the vessel and also allow for maximum plaque volume reduction is to deploy a protective structure such as a stent, thin expandable coil or an expandable mesh 182 within a lesion. As this structure expands after deployment, the thin wire coil or the struts push radially outward through the plaque until it becomes substantially flush with the vessel wall. This expansion of thin members requires minimal displacement of plaque volume and minimizes barotrauma produced in balloon angioplasty or balloon expanded stent delivery. Once the protective structure has expanded fully, atherectomy can be performed to cut away the plaque inside to open up the lumen. The vessel wall is protected by the expanded structure because the structure members (coil or struts) resist cutting by the atherectomy cutter, and are disposed in a way that they cannot invaginate into the cutter housing (and thereby be grabbed by the cutter). It is also possible to adjust the angle of the windows on the atherectomy catheter cutter housing so that they do not align with the struts or coils; the adjustment to orientation may be accounted for in the coil or strut design, in the cutter housing design, or both. Furthermore, the protective member can be relatively flexible and have a low profile (thin elements), so that it may be left in place as a stent. Because the stent in this case relies mainly upon atherectomy to restore lumen patency, it may be designed to exert far less radial force as it is deployed. This allows usage of greater range of materials, some of which may not have as high of stiffness and strength such as bioresorbable polymers and metal alloys. Also, this allows a more resilient design, amenable to the mechanical forces in the peripheral arteries. It also minimizes flow disruption, to minimize hemodynamic complications such as thrombosis related to the relatively low flows found in the periphery. It is also possible to perform atherectomy prior to placing the protective structure, whether or not atherectomy is performed after placing the structure.

Figure 16A:
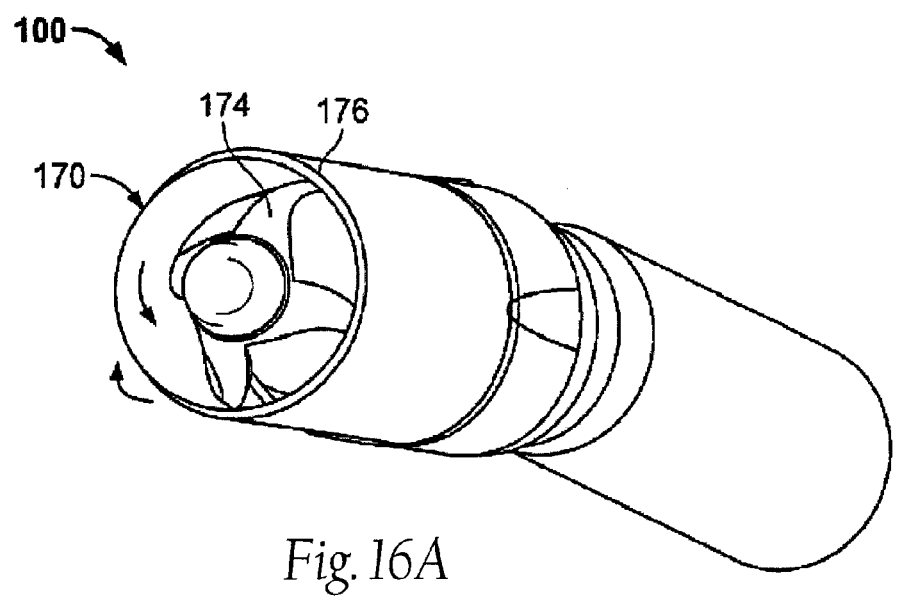
FIGS. 16A-16B show variations of devices for removing tissue from body lumens.
Figure 16B:
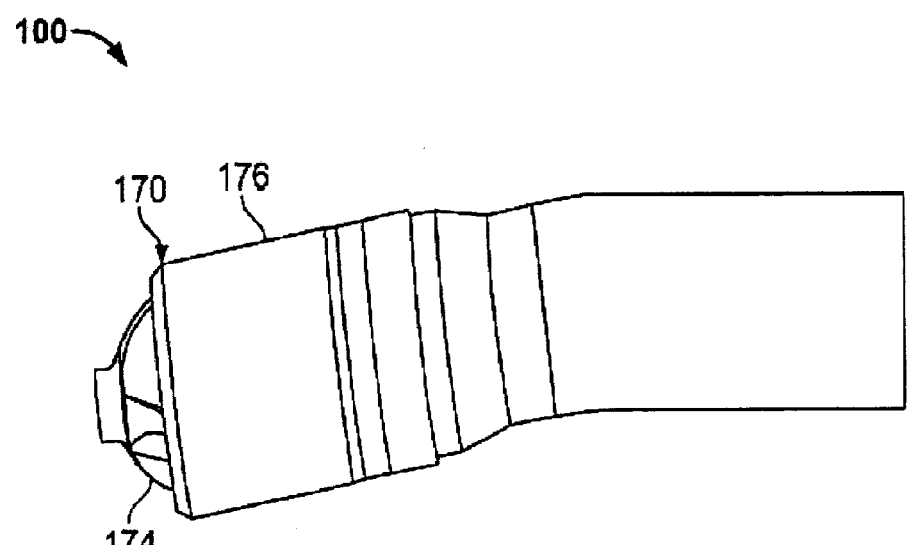
Figure 17A:
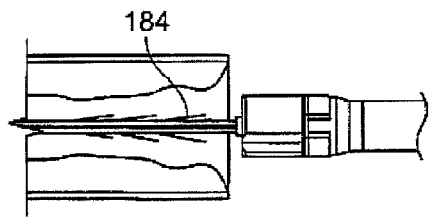
FIGS. 17A-17F show additional variations for centering devices within a lumen.
Figure 17B:
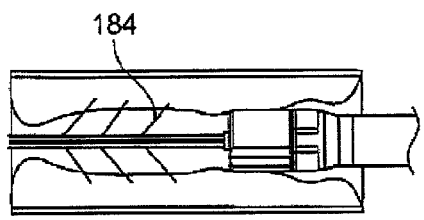
Figure 17C:
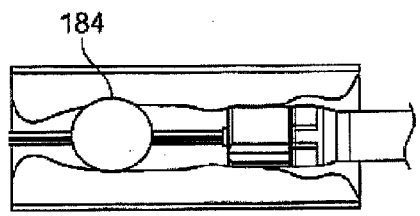
Figure 17D:
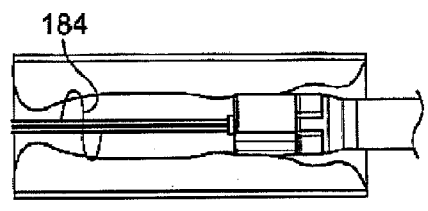
Figure 17E:
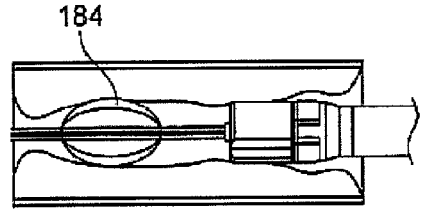
Figure 17F:
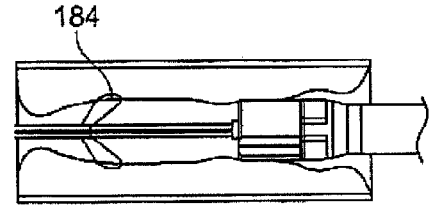

Additional variations of systems include devices 100 having a cutting assembly 170 comprising spinning turbine-like coring cutter 172 as shown above and as shown in FIG. 16A. FIG. 16B shows a side view of the coring cutter 170. In use, the coring cutter can be hydraulically pushed to drive the sharp edge through tissue. The turbine like cutters has helical blades 174 on the inside of the sharp cylinder housing 176 (shell). The coring cutter 170 may also have spokes or centering devices 184 as shown to in FIGS. 17A to 17F center the shell about the guidewire. This helps to keep the cut of the plaque centered about the vessel wall for safety. The spokes also act as an impeller to pull stenotic tissue back and this helps to drive the cutter forward as well as achieve aspiration to minimize embolization.

It is also possible to use the devices and methods described here to restore patency to arterial lesions in the coronary circulation and in the cerebrovascular circulation, both by debulking de novo lesions and by debulking in stent restenosis.

The devices and methods described herein also work particularly well in lesions that are challenging to treat with other methods: at bifurcations, in tortuous arteries, and in arteries which are subject to biomechanical stresses (such as in the knee or other joints).

In a further variation of the devices described here, the motor drive unit may be powered by a controller that varies the speed and torque supplied to the catheter to optimize cutting efficiency or to automatically orbit the cutter using variable speed with a fixed flexible distal length of catheter (or providing further orbiting control by controlling the length of the distal flexible section of the catheter).

It is also possible to use feedback control to operate the catheter in a vessel safe mode, so that the rate of cutting is decreased as the vessel wall is approached. This may be accomplished through speed control, or by reducing the degree to which the cutting blades penetrate above the housing window by retracting the cutter axially within the housing. Feedback variables could be by optical (infrared) or ultrasound transducer, or by other transducers (pressure, electrical impedance, etc.), or by monitoring motor performance. Feedback variables may also be used in safety algorithms to stop the cutter, for example in a torque overload situation.

The atherectomy catheter may be further configured with a balloon proximal to the cutter, for adjunctive angioplasty or stent delivery. The catheter may optionally be configured to deliver self-expanding stents. This provides convenience to the user and greater assurance of adjunctive therapy at the intended location where atherectomy was performed.

Further methods include use of similar devices to debulk stenosis in AV hemodialysis access sites (fistulae and synthetic grafts), as well as to remove thrombus. By removing the cutter housing and recessing the fluted cutter within the catheter sheath, a suitable non-cutting thrombectomy catheter may be constructed.

Other methods of use include excising bone, cartilage, connective tissue, or muscle during minimally invasive surgical procedures. For example, a catheter that includes cutting and burr elements may be used to gain access to the spine for performing laminectomy or facetectomy procedures to alleviate spinal stenosis. For this application, the catheter may be further designed to deploy through a rigid cannula over part of its length, or have a rigid portion itself, to aid in surgical insertion and navigation.

It is advantageous to couple atherectomy with stenting. By removing material, debulking the lesion, a lesser radial force is required to further open the artery and maintain lumen diameter. The amount of debulking can be tuned to perform well in concert with the mechanical characteristics of the selected stent. For stents that supply greater expansion and radial force, relatively less atherectomy is required for satisfactory result. An alternative treatment approach is to debulk the lesion substantially, which will allow placement of a stent optimized for the mechanical conditions inherent in the peripheral anatomy. In essence, the stent can support itself against the vessel wall and supply mild radial force to preserve luminal patency. The stent may be bioresorbable, and/or drug eluting, with the resorption or elution happening over a period for days to up to 12 weeks or more. A period of 4 to 12 weeks matches well with the time course of remodeling and return to stability as seen in the classic wound healing response, and in particular the known remodeling time course of arteries following stent procedures. In addition, the stent geometry can be optimized to minimize thrombosis by inducing swirl in the blood flow. This has the effect of minimizing or eliminating stagnant or recirculating flow that leads to thrombus formation. Spiral construction of at least the proximal (upstream) portion of the stent will achieve this. It is also beneficial to ensure that flow immediately distal to the stent does not create any stagnant or recirculation zones, and swirl is a way to prevent this also.

Any of the atherectomy devices 100 described herein can be used as a tool to treat chronic total occlusions (CTO) or a complete blockage of the artery. The frontward cutting and tip-steering capabilities allows the physician to controllably create a channel through the blockage. In one such method for creating this channel (recanalization) the physician places the device 100 proximal edge of a blockage 10. The following applications contain additional details on such a device useful to treat CTO as well as additional features on various debulking devices. Such patent applications include: U.S. patent application Ser. Nos. 11/551,191, 11/551,193, 11/551,198, and 11/551,203 each filed Oct. 19, 2006; U.S. patent application Ser. No. 11/567,715 filed Dec. 6, 2006; U.S. patent application Ser. No. 11/771,865 filed Jun. 29, 2007; and U.S. Provisional Application No. 60/981,735 filed Oct. 22, 2007 each of which is incorporated by reference.

Figure 18A:
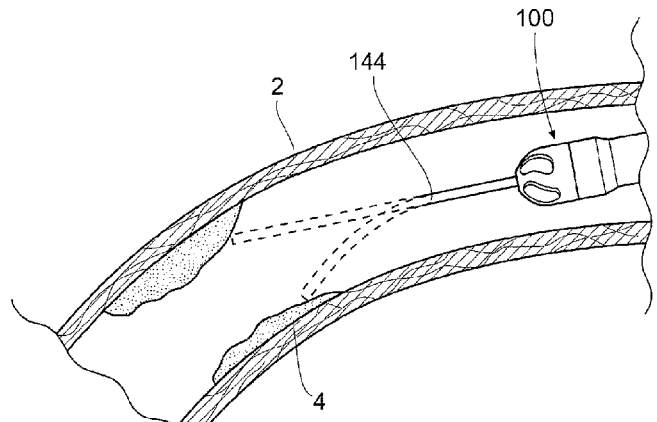
FIGS. 18A-18C illustrate use of a debulking device to assist in the navigation of a guidewire through tortuous anatomy.
Figure 18B:
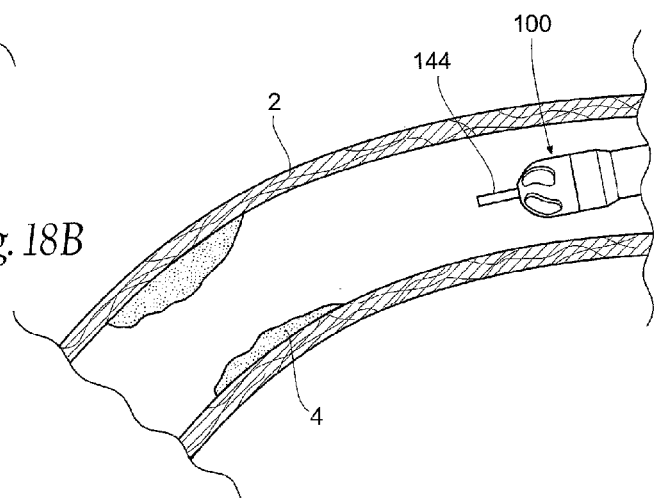
Figure 18C:
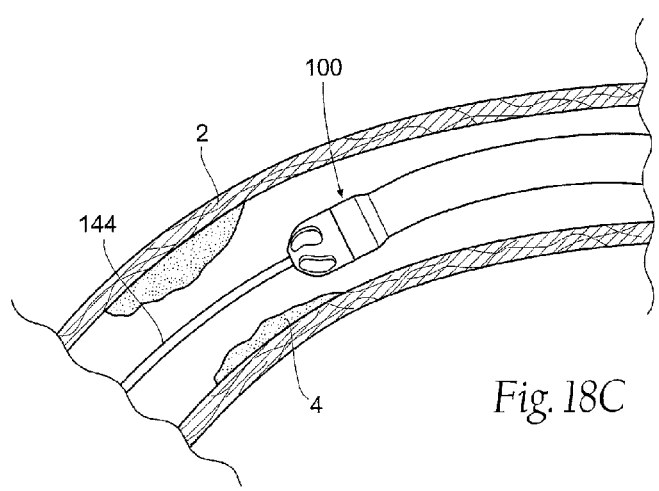

In another variation of the invention, the steerable debulking device 100 can improve the ability of a physician attempting to navigate a guidewire 144 through branching, tortuous or otherwise obstructed anatomy. In the variation shown in FIG. 18A, as a physician navigates a guidewire 144 through the anatomy, the tortuous nature of the anatomy or obstructions 4 within the vessel 2 may prevent advancement of the guidewire 144 as shown. In such a case, the steerable debulking device 100 of the present invention permits a physician to withdraw the guidewire within or just distal to the debulking device 100 (as shown in FIG. 18B.) The device 100 can then be advanced to a branching point or beyond the tortuous location or obstruction, and articulated (as shown in FIG. 18C) so that the physician can then advance the guidewire 144 beyond the obstruction, sharp bend or into the desired branch.

It is noted that the descriptions above are intended to provide exemplary embodiments of the devices and methods. It is understood that, the invention includes combinations of aspects of embodiments or combinations of the embodiments themselves. Such variations and combinations are within the scope of this disclosure.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A device for removing material from a body lumen, the device comprising:
    a catheter having a proximal end, a distal end, and a catheter lumen extending therethrough;
    a cutter assembly located at the distal end of the catheter;
    a torque shaft extending through the catheter lumen and attached to the cutter assembly for rotating a cutter of the cutter assembly;
    a sweep frame positioned coaxially with respect to the distal end of the catheter and coupled to the cutter assembly such that the cutter assembly prevents the sweep frame from moving distally, the sweep frame comprising a weakened section on a first radial side such that compression of the sweep frame causes deflection towards the first radial side;
    sweep member coupled to the sweep frame, the sweep member comprising a tubular structure axially moveable within the catheter and having sufficient column strength to compress and rotate the sweep frame; and
    a sweep control knob coupled to the sweep member and rotatable independently relative to the torque shaft, the sweep control knob configured to, when axially advanced and rotated, sweep the cutter assembly in an arc manner.

2. The device of claim 1 further comprising a lumen extending through the torque shaft and the cutter accommodating passage of a guide wire.

3. The device of claim 1 wherein the cutter comprises a plurality of cutting flutes.

4. The device of claim 3 where an edge of each of the cutting flutes is helical.

5. The device of claim 1 wherein the torque shaft has at least one helical conveyor member wound about an exterior such that rotation of the torque shaft conveys material across a length of the torque shaft.

6. The device of claim 1 further comprising a guide wire.

7. The device of claim 1 further comprising a burr rotatably located on a tip of the cutter assembly.

* * * * *